United States Patent [19]

Suchy et al.

[11] Patent Number: 5,041,156

[45] Date of Patent: Aug. 20, 1991

[54] 3-ARYLURACILS FOR THE CONTROL OF WEEDS

[75] Inventors: Milos Suchy, Pfaffhausen; Jean Wenger, Uster; Paul Winternitz, Greifensee; Martin Zeller, Dübendorf, all of Switzerland

[73] Assignee: Ciba-Geigy Corporation, Ardsley, N.Y.

[21] Appl. No.: 369,557

[22] PCT Filed: Oct. 21, 1988

[86] PCT No.: PCT/CH88/00197

§ 371 Date: Jun. 16, 1989

§ 102(e) Date: Jun. 16, 1989

[87] PCT Pub. No.: WO89/03825

PCT Pub. Date: May 5, 1989

[30] Foreign Application Priority Data

Oct. 22, 1987 [CH] Switzerland .................. 4132/87

[51] Int. Cl.[5] .................. A01N 43/48; C07D 239/02
[52] U.S. Cl. .................................. 71/92; 544/309; 544/311; 544/312; 544/313
[58] Field of Search ............... 544/309, 311, 312, 313; 71/92

[56] References Cited

U.S. PATENT DOCUMENTS

| 3,137,698 | 6/1964 | Pfister | 544/309 |
| 4,266,056 | 5/1981 | Henrick et al. | 544/311 |
| 4,812,164 | 3/1989 | Wenger et al. | 544/309 |
| 4,859,229 | 8/1989 | Wenger et al. | 544/309 |
| 4,927,451 | 5/1990 | Brouwer et al. | 544/309 |

OTHER PUBLICATIONS

March, Advanced Organic Chemistry, 3rd Edition, pp. 348-352.

Primary Examiner—Cecilia Shen
Attorney, Agent, or Firm—Edward McC. Roberts

[57] ABSTRACT

The present invention is concerned with heterocyclic compounds, namely 3-aryluracils of the general formula

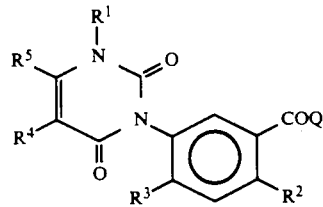

wherein $R^1$, $R^2$, $R^3$, $R^4$, $R^5$ and Q are as described herein, as well as salts thereof and their manufacture, weed control compositions.

11 Claims, No Drawings

3-ARYLURACILS FOR THE CONTROL OF WEEDS

The present invention is concerned with heterocyclic compounds, namely 3-aryluracils of the general formula I

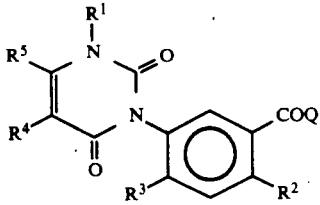

wherein
$R^1$ signifies hydrogen, $C_{1-4}$-alkyl, $C_{1-4}$-haloalkyl, $C_{2-5}$-alkenyl or $C_{3-5}$-alkynyl,
$R^2$ signifies halogen or cyano,
$R^3$ signifies hydrogen or halogen,
$R^4$ signifies hydrogen, halogen or $C_{1-4}$-alkyl,
$R^5$ signifies $C_{1-4}$-alkyl or, where $R^1$ is different from $C_{1-4}$-haloalkyl, also $C_{1-4}$-haloalkyl
Q signifies one of the groups (a) to (d) (where $R^1$ is different from hydrogen) or a group (c) or (d) (where $R^1$ stands for hydrogen)

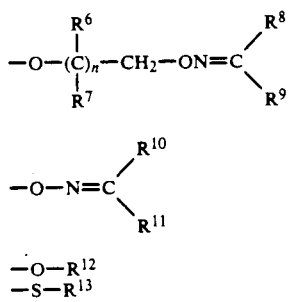

wherein
$R^6$ signifies hydrogen or $C_{1-4}$-alkyl,
$R^7$ signifies hydrogen, $C_{1-4}$-alkyl, phenyl or benzyl,
$R^8$ signifies hydrogen or $C_{1-6}$-alkyl,
$R^9$ signifies $C_{1-6}$-alkyl, $C_{3-6}$-cycloalkyl or phenyl. or
$R^8$ and $R^9$ together signify tri-, tetra-, penta- or hexamethylene,
n signifies 0 or 1,
$R^{10}$ signifies $C_{1-6}$-alkyl, $C_{1-6}$-alkylthio, $C_{2-7}$-alkoxycarbonyl or $C_{2-7}$-alkoxycarbonyl-$C_{1-4}$-alkyl,
$R^{11}$ signifies $C_{1-6}$-alkyl, trifluoromethyl, $C_{1-6}$-alkoxy-$C_{1-4}$-alkyl, $C_{2-7}$-alkoxycarbonyl-$C_{1-4}$-alkyl, di ($C_{2-7}$-alkoxycarbonyl)-$C_{1-4}$-alkyl, $C_{3-6}$-cycloalkyl, $C_{1-6}$-alkoxy, $C_{1-6}$-alkylthio, $C_{2-7}$-alkanoyl, $C_{2-7}$-alkoxycarbonyl, phenyl or 2-furyl,
or
$R^{10}$ and $R^{11}$ together with the carbon atom to which they are attached signify a cyclopentane or cyclohexane ring optionally substituted with 1 to 3 $C_{1-4}$-alkyl groups,
$R^{12}$ signifies $C_{1-8}$-haloalkyl, $C_{3-5}$-haloalkenyl or $C_{3-5}$-haloalkynyl,
and
$R^{13}$ signifies hydrogen, $C_{1-8}$-alkyl, $C_{3-8}$-alkenyl, $C_{3-8}$-alkynyl. $C_{2-6}$-alkoxyalkyl or $C_{3-8}$-cycloalkyl, phenyl or benzyl optionally
substituted with 1 to 3 $C_{1-4}$-alkyl groups, and the enol ethers of those compounds of formula I in which $R^1$ signifies $C_{1-4}$-alkyl $C_{2-5}$-alkenyl or $C_{3-5}$-alkynyl and Q signifies a group (b), (c) or (d) as well as salts of those compounds of formula I and of the enol ethers in which $R^1$ and/or $R^{13}$ signifies hydrogen.

Under the above-mentioned enol ethers there are thus to be understood the compounds of the formula

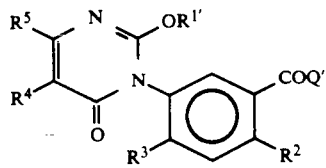

and also the compounds of the formula

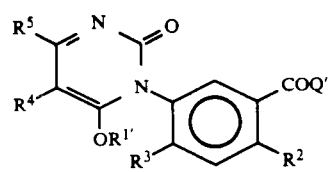

wherein $R^2$, $R^3$, $R^4$ and $R^5$ have the significances given above, R signifies $C_{1-4}$-alkyl, $C_{2-5}$-alkenyl or $C_{3-5}$-alkynyl and Q' signifies a group (b). (c) or (d). Their salts are salts of those enol ethers Ia and Ib in which Q' signifies mercapto, i.e. group (d) in which signifies hydrogen.

The compounds in accordance with the invention. i.e. the compounds of formula I and their enol ethers and the salts thereof. have herbicidal activity and are suitable as active substances of weed control compositions. Accordingly, the invention also embraces weed control compositions which contain compounds in accordance with the invention as the active substance, a process for the manufacture of these compounds as well as the use of the compounds or compositions for the control of weeds.

In formula I above "halogen" embraces fluorine, chlorine, bromine and iodine. The alkyl, alkenyl and alkynyl residues can be straight-chain or branched and this also applies to the or each alkyl, alkenyl or alkynyl part of the haloalkyl, alkylthio, alkoxycarbonyl, alkoxycarbonylalkyl, alkoxyalkyl, dialkoxycarbonylalkyl, alkoxy, alkanoyl, haloalkenyl and haloalkynyl qroups. A haloalkyl, haloalkenyl or haloalkynyl group can have one or more (similar or different) halogen atoms. Likewise, a cyclopentyl, cyclohexyl, $C_{3-8}$-cycloalkyl, phenyl or benzyl group multiply substituted with $C_{1-4}$-alkyl groups can have the same or different alkyl substituents.

The salts of the compounds of formula I and of the enol ethers of formulae Ia and Ib are especially alkali metal salts, e.g. sodium and potassium salts; alkaline earth metal salts, e.g. calcium and magnesium salts; ammonium salts. i.e. unsubstituted ammonium salts and mono- or multiply-substituted ammonium salts, e.g. triethylammonium and methylammonium salts, as well as salts with other organic bases, e.g. with pyridine.

The presence of at least one asymmetric carbon atom in the compounds I and in their enol ethers Ia and Ib means that the compounds can occur in optically isomeric forms. Geometric isomerism can also occur when an aliphatic C=C or C=N double bond is present. Moreover. in those compounds of formula I in which $R^1$ signifies hydrogen keto-enol tautomerism [—N-

H—CO—⇌—N=C(OH)—] can occur. Formula I is intended to embrace all of these possible isomeric forms as well as mixtures thereof.

When $R^1$ or $R^{13}$ signifies alkenyl or alkynyl, this residue is preferably allyl or propargyl, respectively. A haloalkyl group which may be present is preferably $C_{1-4}$-fluoroalkyl. especially difluoromethyl in the case of $R^1$ and trifluoromethyl or pentafluoroethyl in the case of $R^5$ In general, a halogen atom which may be present is preferably fluorine, chlorine or bromine.

A particular group of compounds of formula I comprises those compounds I in which R signifies $C_{1-4}$-alkyl or $C_{1-4}$-haloalkyl. $R^2$ signifies halogen, $R^4$ signifies hydrogen and Q signifies a group (a) in which $R^6$ signifies hydrogen, $R^7$ signifies hydrogen, $C_{1-4}$-alkyl or phenyl, $R^8$ signifies $C_{1-6}$-alkyl, $R^9$ signifies $C_{1-6}$-alkyl, $C_{3-6}$-cycloalkyl or phenyl, or $R^8$ and $R^9$ together signify —$(CH_2)_{3-6}$- and n signifies 1, or Q signifies a group (b) in which signifies $C_{1-6}$-alkyl or $C_{2-7}$-alkoxycarbonyl-$C_{1-4}$-alkyl and $R^{11}$ signifies $C_{1-6}$-alkyl, trifluoromethyl, $C_{1-6}$-alkoxy-$C_{1-4}$-alkyl, $C_{2-7}$-alkoxycarbonyl-$C_{1-4}$-alkyl, $C_{3-7}$-cycloalkyl, $C_{1-6}$-alkoxy. $C_{2-7}$-alkanoyl. $C_{2-7}$-alkoxycarbonyl, phenyl or 2-furyl, or $CR^{10}R^{11}$ signifies a cyclopentane or cyclohexane ring, or Q signifies a group (c), as defined above, or Q signifies a group (d) in which $R^{13}$ signifies $C_{1-8}$-alkyl, $C_{3-8}$-alkenyl, $C_{3-8}$-cycloalkyl. phenyl or benzyl, and their enol ethers.

Independently of each other $R^1$ preferably signifies straight-chain $C_{1-4}$-alkyl, especially methyl, or difluoromethyl; $R^2$ preferably signifies chlorine or bromine; $R^3$ preferably signifies hydrogen or fluorine; $R^4$ preferably signifies hydrogen, fluorine or methyl; and $R^5$ preferably signifies methyl, trifluoromethyl or pentafluoroethyl.

Especially preferred individual compounds in accordance with the invention are:

2-[(Isopropylideneamino)oxy]-ethyl 2-chloro-5-[3,6-dihydro-2,6-dioxo-3-methyl-4-trifluoromethyl-1(2H)-pyrimidinyl]-4-fluorobenzoate, 2-[(cyclohexylideneamino)oxy]-ethyl 2-chloro-5-[3,6-dihydro-2,6-dioxo-3-methyl-4-trifluoromethyl-1(2H)-pyrimidinyl]-4-fluorobenzoate, α-{[(isopropylideneamino)oxy]methyl}-benzyl 2-chloro-5-[3,6-dihydro-2,6-dioxo-3-methyl-4-trifluoromethyl-1(2H)-pyrimidinyl]-4-fluorobenzoate, 1-cyclopropyl-1-ethanone O-{2-chloro-5-[3,6-dihydro2,6-dioxo-3-methyl-4-trifluoromethyl-1(2H)-pyrimidinyl]-4-fluorobenzoy1}oxime, 1-[4-chloro-2-fluoro-5-{[(isopropylideneamino)oxy]carbonyl}-phenyl]-3-methyl-4-trifluoromethyl-2,6(1H,3H)-pyrimidinedione.

2-furyl methyl ketone O-{2-chloro-5-[3,6-dihydro-2,6-dioxo-3-methyl-4-trifluoromethyl-1(2H)-pyrimidinyl]-4-fluorobenzoyl]oxime, 2,3-butanedione 2-[O-[2-chloro-5-[3,6-dihydro-2,6-dioxo-3-methyl-4-trifluoromethyl-1(2H)-pyrimidinyl]-4-fluorobenzoyl}]oxime, 2-fluoro-1-fluoromethylethyl 2-chloro-4-fluoro-5-[2-methoxy-6 oxo-4-trifluoromethyl-1(6H)-pyrimidinyl]-benzoate, 2-chloroethyl 2-chloro-4-fluoro-5-[2-methoxy-6-oxo-4-trifluoromethyl-1(6H)-pyrimidinyl]-benzoate, 2-fluoroethyl 2-chloro-5-[3,6-dihydro-2,6-dioxo-3-methyl-4-trifluoromethyl-1(2H)-pyrimidinyl]-4-fluorobenzoate 3-chloro-2-butenyl 2-chloro-4-fluoro-5-[2-methoxy-6-oxo-4-trifluoromethyl-1(6H)-pyrimidinyl]-benzoate.

3-chloro-2-butenyl 2-chloro-5-[3,6-dihydro-2,6-dioxo-3-methyl-4-trifluoromethyl-1(2H)-pyrimidinyl]-4-fluorobenzoate, 2-fluoroethyl 2-chloro-4-fluoro-5-[2-methoxy-6-oxo-4-trifluoromethyl-1(6H)-pyrimidinyl]-benzoate, S-isopropyl 2-chloro-5-[3,6-dihydro-2,6-dioxo-3-methyl-4-trifluoromethyl-1(2H)-pyrimidinyl]-4-fluorothiobenzoate, S-ethyl 2-chloro-5-[3,6-dihydro-2,6-dioxo-3-methyl-4-trifluoromethyl-1(2H)-pyrimidinyl]-4-fluorothiobenzoate, S-(n-butyl) 2-chloro-5-[3,6-dihydro-2,6-dioxo-3-methyl-4-trifluoromethyl-1(2H)-pyrimidinyl]-4-fluorothiobenzoate.

S-allyl 2-chloro-5-[3,6-dihydro-2,6-dioxo-3-methyl-4-trifluoromethyl-1(2H)-pyrimidinyl]-4-fluorothiobenzoate, S-cyclohexyl 2-chloro-5-[3,6-dihydro-2,6-dioxo-3-methyl-4-trifluoromethyl-1(2H)-pyrimidinyl]-4-fluorothiobenzoate, S-phenyl 2-chloro-5-[3,6-dihydro-2,6-dioxo-3-methyl-4-trifluoromethyl-1(2H)-pyrimidinyl]-4-fluorothiobenzoate, S-benzyl 2-chloro-5-[3,6-dihydro-2,6-dioxo-3-methyl-4-trifluoromethyl-1(2H)-pyrimidinyl]-4-fluorothiobenzoate and S-isopropyl 2-chloro-5-[3,6-dihydro-3.4-dimethyl-2,6-dioxo-1(2H)-pyrimidinyl]-4-fluorothiobenzoate.

Further representatives of compounds of formula I are those compounds I in which $R^1$ and $R^5$ each signify methyl. $R^2$ signifies chlorine. $R^3$ signifies fluroine, $R^4$ signifies hydrogen, Q signifies a group (a), $R^6$ and $R^7$ signifies hydrogen, n signifies 1 and $CR^8R^9$ signifies sec.butylidene, 1-isopropylethylidene, 1-ethylpropylidene, 1-isopropylpropylidene. 1-propylethylidene, 1-propylpropylidene, 1-propylbutylidene, 1-butylethylidene 1-cyclopropylethylidene. 1-phenylethylidene. cyclopentylidene or cyclohexylidene: 1-methyl-2-[isopropylideneamino)oxy]-ethyl 2-chloro-5-[3,6-dihydro3,4-dimethyl-2 6-dioxo-1(2H)-pyrimidinyl]-4-fluorobenzoate; 2-[(isopropylideneamino)oxy]-ethyl 5-[4-ethyl-3 6-dihydro2,6-dioxo-3-methyl-1(2H)-pyrimidinyl]-2-chloro-4-fluorobenzoate; 2-[(isopropylideneamino)oxy]-ethyl 2-chloro-5-[3,6-dihydro-3,4-dimethyl-2,6-dioxo-1(2H)-pyrimidinyl]-benzoate; 2-[(sec.-butylideneamino)oxy]-ethyl 2-chloro-5-[3-difluoromethyl-3,6-dihydro-2,6-dioxo-4-methyl-1(2H)-pyrimidinyl]-4-fluorobenzoate; 2-[(1-ethylpropylideneamino)oxy]-ethyl 2-chloro-5-[3-difluoromethyl-3 6-dihydro-2 6-dioxo-4-methyl-1(2H)-pyrimidinyl]-4-fluorobenzoate; 2-[(isopropylideneamino)oxy]-ethyl 2-chloro-5-[3-difluoromethyl-3,6-dihydro-2,6-dioxo-4-methyl-1(2H)-pyrimidinyl]benzoate; those compounds I in which $R^1$ and $R^5$ each signify methyl, $R^2$ signifies chlorine, $R^3$ signifies fluorine, $R^4$ signifies hydrogen, Q signifies a group (b) and signifies sec.butylidene, 1-isopropylethylidene, 1-ethylpropylidene, 1-isopropylpropylidene, 1-propylethylidene, 1-propylpropylidene, 1-propylbutylidene, 1-butylethylidene, 1-cyclopropylethylidene, 1-phenylethylidene cyclopentylidene or cyclohexylidene: acetone O-5-[4-ethyl-3,6-dihydro-2 6-dioxo-3-methyl-1(2H)-pyrimidinyl]-2-chloro-4-fluorobenzoyl-}oxime: acetone O-{2-chloro-5-[3,6-dihydro-3,4-dimethyl-2,6-dioxo-1(2H)-pyrimidinyl]-benzoyl}oxime; 1,1,1-trifluoroacetone O-[2-chloro-5-[3 6-dihydro-3,4-dimethyl-2,6-dioxo-1(2H)-pyrimidinyl]-4-fluorobenzoyl}oxime; methylacetate O-[2-chloro-5-[3,6-dihydro- 3,4-dimethyl-2,6-dioxo-1(2H)-pyrimidinyl]-4-fluorobenzoyl}oxime; acetone-O-{2-chloro-5-[3-difluoromethyl-3,6-dihydro-2,6-dioxo-4-methyl-1(2H)-pyrimidinyl]-4-fluorobenzoyl}oxime; 2-butanone 0-{2-chloro-5-[3-difluoromethyl-3,6-dihydro-2,6-dioxo-4-methyl-1(2H)-pyrimidinyl]-4-fluorobenzoyl}oxime; acetone 0-{2-chloro-5-[3-difluoro-methyl-3,6-dihydro-2,6-dioxo-4-methyl-1(2H)-pyrimidinyl]-benzoyl}oxime; those compounds I in which $R^1$ and $R^5$ each signify methyl, $R^2$ signifies chlorine, $R^3$ signifies fluorine, $R^4$ signifies hydrogen, Q signifies a group (c) and $R^{12}$ signifies 2-chloro-1-methylethyl, 2-fluoroethyl, 2-bromoethyl, di(chloromethyl)methyl, di(fluoromethyl)methyl. 3,3-dibromo-2-propenyl, 3-chloro-2-butenyl, 4-chloro-2-butenyl, 4-bromo-2-butenyl, 2,2,2-trifluoroethyl, 4-chlorobutyl, 2-chloro-2-propenyl, di(trifluoromethyl)-methyl, 3-chloro-2-propynyl or 3-chloro-2-butenyl; 2-chloroethyl 2-chloro-5-[3,6-dihydro-3,4-dimethyl-2,6-dioxo-1(2H)-pyrimidinyl]-benzoate; 2-chloroethyl 5-[4-ethyl-3,6-dihydro-2,6-dioxo-3-methyl-1(2H)-pyrimidinyl]-2-chloro-4-fluorobenzoate; those compounds I in which $R^1$ signifies methyl, $R^2$ signifies chlorine, $R^3$ signifies fluorine, $R^4$ signifies hydrogen, $R^5$ signifies trifluoromethyl, Q signifies a group (d) and $R^{13}$ signifies n-propyl, sec.butyl or cyclopentyl; those compounds I in which $R^1$ and $R^5$ each signify methyl, $R^2$ signifies chlorine, $R^3$ signifies fluorine, $R^4$ signifies hydrogen. Q signifies a group (d) and $R^{13}$ signifies ethyl isopropyl, allyl, cyclopentyl or cyclohexyl; isopropyl 2-chloro-5-[3 6-dihydro-2,6-dioxo-3-methyl-4-trifluoromethyl-1(2H)-pyrimidinyl]-thiobenzoate; allyl 2-chloro-5-[3,6-dihydro-2,6-dioxo-3-methyl-4-trifluoromethyl-1(2H)-pyrimidinyl]-thiobenzoate; and those compounds I in which $R^1$ signifies difluoromethyl. $R^2$ signifies chlorine, $R^3$ signifies fluorine, $R^4$ signifies hydrogen, $R^5$ signifies methyl, Q signifies a group (d) and $R^{13}$ signifies ethyl, tert.butyl, allyl, cyclopentyl or cyclohexyl.

The process in accordance with the invention for the manufacture of the compounds of formula I and their enol ethers as well as salts is characterized by (a) for the manufacture of those compounds of formula I in which $R^1$ signifies hydrogen and Q signifies a group (c) or (d) as well as, if desired, of metal salts of these compounds, subjecting a compound of the general formula

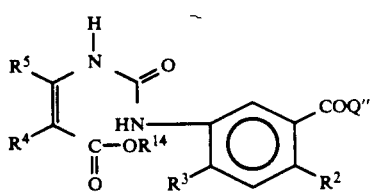

wherein $R^2$, $R^3$, $R^4$ and $R^5$ have the significances given above, Q" signifies a group (c) or (d), as defined above, and $R^{14}$ signifies lower alkyl, preferably $C_{1-4}$-alkyl, to a cyclization under basic conditions and, if desired, converting a metal salt of the uracil derivative of formula I which may be obtained into the acidic form ($R^1$ = hydrogen) by treatment with an acid, (b) for the manufacture of those compounds of formula I in which $R^1$ signifies $C_{1-4}$-alkyl, $C_{1-4}$-haloalkyl, $C_{2-5}$-alkenyl or $C_{3-5}$-alkynyl and Q signifies one of the groups (a) to (d) and of the enol ethers of these compounds, esterifying a benzoic acid of the general formula

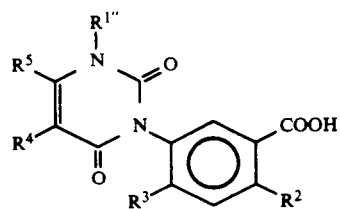

wherein $R^2$, $R^3$, $R^4$ and $R^5$ have the significances given above and $R^{1''}$ signifies $C_{1-4}$-alkyl, $C_{1-4}$-haloalkyl, $C_{2-5}$-alkenyl or $C_{3-5}$-alkynyl, or a reactive derivative of this benzoic acid with a hydroxy or mercapto compound of the general formula $$H—Q \qquad IV$$

wherein Q has the significance given above, or with a reactive derivative of this hydroxy or mercapto compound or esterifying an enol ether of this benzoic namely of the general formula

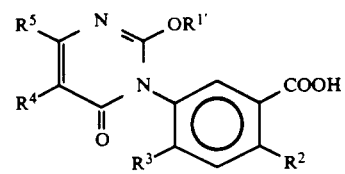

or

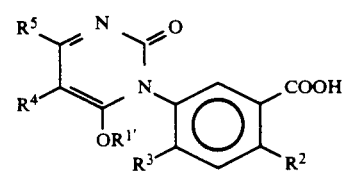

wherein $R^{1'}$, $R^2$, $R^3$, $R^4$ and $R^5$ have the significances given above, or a reactive derivative of this enol ether with a hydroxy or mercapto compound of the general formula $$H—Q' \qquad IV'$$

wherein Q' has the significance given above, or with a reactive derivative of this hydroxy or mercapto compound, (c) for the manufacture of those compounds of formula I in which $R^1$ signifies $C_{1-4}$-alkyl, $C_{1-4}$-haloalkyl, $C_{2-5}$-alkenyl or $C_{3-5}$-alkynyl and Q signifies a group (c), subjecting a benzoic acid ester of the general formula

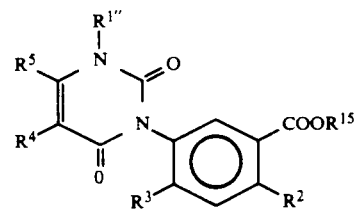

wherein $R^{1''}$, $R^2$, $R^3$, $R^4$ and $R^5$ have the significances given above and $R^{15}$ signifies $C_{1-6}$-alkyl, $C_{2-4}$-alkenyl, $C_{2-4}$-alkynyl or $C_{2-6}$-alkoxyalkyl, to a trans-esterification reaction with a hydroxy compound of the general formula $$H-Q''' \qquad \qquad IV''0$$

wherein $Q'''$ signifies a group (c). whereby the reagent IV''' has a higher boiling point than the hydroxy compound $R^{15}OH$ formed, or (d) for the manufacture of those enol ethers of formula Ia and Ib in which $Q'$ signifies a group (c) or (d), treating a pyrimidinone derivative of the general formula

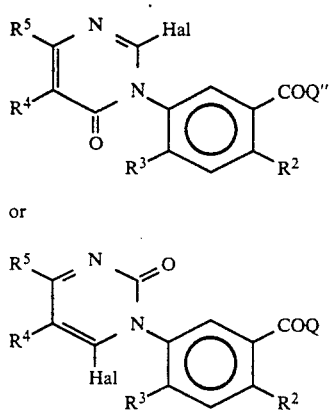

wherein $R^2$, $R^3$, $R^4$, $R^5$ and $Q''$ have the significances given above and Hal signifies chlorine or bromine, with the deprotonized form of an alkanol, alkenol or alkynol $R^{1'}OH$ in which $R^{1'}$ has the significance given above. and if desired, converting a thus-obtained compound of mula I in which $R^1$ and/or $R^{13}$ signifies hydrogen into a salt.

The cyclization according to process variant (a) can be carried out conveniently by treating the compound of formula II in an inert protic organic solvent such as an alcohol, e.g. methanol. ethanol or isopropanol; an inert aprotic organic solvent such as an aliphatic or cyclic ether, e.g. 1,2-dimethoxyethane, tetrahydrofuran or dioxan, or an aromatic, e.g. benzene or toluene; an inert aprotic, polar organic solvent, e.g. dimethylformamide or dimethyl sulphoxide, whereby such solvents can be used, if desired-in a two-phase mixture with a hydrocarbon, e.g. n-hexane or toluene; or water with a base at temperatures between $-78°$ C. and the reflux temperature of the reaction mixture. As bases there preferably come into consideration sodium alcoholates, alkali metal hydroxides, especially sodium hydroxide and potassium hydroxide alkali metal carbonates. especially sodium carbonate and potassium carbonate, and sodium hydride. When sodium hydride is used as the base, the solvent is preferably an aliphatic or cyclic ether, dimethylformamide or dimethyl sulphoxide, whereby any of these solvents can be used in admixture with toluene.

After completion of the cyclization the product. when one of the above-mentioned bases or the like is used, is present in the form of the corresponding alkali metal salt. This can be isolated and purified in a manner known per se or the mixture can be acidified in order to isolate the respective compound of formula I itself. A mineral acid such as hydrochloric acid or a strong organic acid such as acetic acid or p-toluenesulphonic acid is preferably used for this purpose.

Process variant (b) is an esterification of the benzoic acid III or of the enol ether IIIa or IIIb or of a reactive derivative of the benzoic acid or of the enol ether, which can be carried out according to methods known per se. Thus, for example, a salt of a benzoic acid of formula III or of the enol ether IIIa or IIIb is reacted with a halide, especially chloride, bromide or iodide, or the sulphate, mesylate or tosylate of the hydroxy or mercapto compound IV or, respectively, IV' in an inert diluent at temperatures between room temperature and 100° C., e.g. at the reflux temperature of the reaction mixture, preferably in the temperature range of 40° C. to 70° C. As salts of the benzoic acid of formula III or of the corresponding enol ether there especially come into consideration alkali metal salts, e.g. the lithium, sodium and potassium salt, alkaline earth metal salts, e.g. the calcium, magnesium and barium salt, and salts with organic bases such as tertiary amines, e.g. triethylamine, 1,5-diaza-bicyclo[4,3,0]non-5-ene, 1,8-diazabicyclo[5,4,0]undec-7-ene and 1,4-diaza-bicyclo[2,2,-2]octane, with the alkali metal salts, especially the sodium salt and the potassium salt, being preferred. As diluents there are preferably used inert organic solvents such as lower alkanols, e.g. ethanol, aliphatic and cyclic ethers, e.g. diethyl ether, tetrahydrofuran and dioxan, ketones, e.g. acetone and 2-butanone, dimethylformamide, dimethyl sulphoxide and hexamethylphosphoric acid triamide. The salt can be produced in situ by converting the acid with a suitable inorganic base, e.g. an alkali metal or alkaline earth metal carbonate or bicarbonate or an alkali metal hydride or organic base into the salt and subsequently letting this react in the same reaction medium with the second reaction partner.

When an acid halide of the benzoic acid of formula III or of the enol ether IIIa or IIIb is used as the reactive derivative, this is conveniently reacted with the hydroxy or mercapto compound IV or IV' in an inert organic solvent such as an aliphatic or cyclic ether, e.g. diethyl ether, tetrahydrofuran or dioxan, an aliphatic or aromatic hydrocarbon, e.g. n-hexane, benzene or toluene, or a halogenated, especially chlorinated, hydrocarbon, e.g. methylene chloride, chloroform or carbon tetrachloride, at temperatures from about $-20°$ C. to 100° C. preferably from 0° C. to 50° C. Moreover, the reaction is conveniently carried out in the presence of an acid-binding agent such as an organic base, e.g. triethylamine, pyridine, 1,5-diaza-bicyclo[4.3.0]non-5-ene, 1,8-diazabicyclo[5.4.0]undec-7-ene or 1,4-diaza-bicyclo[2.2.2]octane. The acid halide is preferably the acid chloride.

As further reactive derivatives of the benzoic acid III or of the enol ether IIIa or IIIb which come into consideration there are to be named the corresponding O-acyl-1,3-dicyclohexylisourea, which is conveniently formed in situ by treating the benzoic acid III or the enol ether IIIa or IIIb with dicyclohexylcarbodiimide, and the corresponding N-acylimidazole or acid anhydride. Such derivatives can be reacted like the acid halide with the hydroxy or mercapto compounds IV or IV' in order to obtain the desired benzoic acid esters. In these cases, however, the use of an acid-binding agent is unnecessary.

The reaction according to process variant (c) can be carried out conveniently by heating the benzoic acid ester of formula V in excess hydroxy compound of formula IV‴ in the presence of a basic catalyst, e.g. sodium cyanide, preferably at the reflux temperature of the reaction mixture. In the course of the reaction the residue $R^{15}$ of the benzoic acid ester V is replaced by the group Q‴ (c) of the hydroxy compound IV‴, whereby the alkanol, alkenol or alkynol $R^{15}OH$ which has a lower boiling point is liberated.

The deprotonized form of the alkanol, alkenol or alkynol $R^{1}OH$ which is used in process variant (d) is conveniently produced either by using the hydroxy compound $R^{1}OH$ in the presence of an organic base, especially an organic tertiary base, e.g. trierhylamine or pyridine, or the corresponding metal alkanolate, alkenolate or alkynolate $R^{1}O^{\ominus}M^{\oplus}$ in which $M^{\ominus}$ signifies an equivalent of a metal ion such as an alkali metal ion, e.g. sodium or potassium or an alkaline earth metal ion, e.g. calcium or magnesium. The sodium ion is the preferred metal ion.

The reaction is conveniently effected in an excess of the corresponding hydroxy compound $R^{1}OH$ as the diluent and at temperatures between 0° C. and 50° C., preferably at room temperature.

Insofar as they are not manufactured directly by the above-described cyclization which is carried out under basic conditions, the desired salts of the compounds of formula I in which $R^1$ and/or $R^{13}$ signifies hydrogen as well as of the enol ethers of formulae Ia and Ib in which $R^{13}$ signifies hydrogen can also be manufactured from these compounds in a manner known per se such as, for example, by dissolving the compound I or the enol ether Ia or Ib in a solution of a respective inorganic or organic base. The salt formation is generally effected within a short time at room temperature. In one embodiment the sodium salt is manufactured by dissolving the compound I or the enol ether Ia or Ib in aqueous sodium hydroxide solution at room temperature, with equivalent amounts of the compound I or of the enol ether Ia or Ib and of sodium hydroxide being used. The solid salt can be isolated by precipitation with a suitable inert solvent or by evaporation of the solvent. A further embodiment comprises introducing an aqueous solution of an alkali metal salt of the compound I or of the enol ether Ia or Ib into an aqueous solution of a salt which has a metal ion other than an alkali metal ion, whereby the second metal salt of the compound or of the enol ether is manufactured. This embodiment is generally used for the manufacture of those metal salts which are insoluble in water.

The resulting compounds of formula I, enol ethers as well as salts can be isolated and purified according to known methods. Insofar as no planned synthesis for the isolation of pure isomers is carried out, the product can result as a mixture of two or more isomers. The isomers can be separated according to methods known per se. If desired, pure optically active isomers can also be manufactured by synthesis from corresponding optically active starting materials.

The starting materials of formula II are novel and can be produced in a manner known per se, e.g. in accordance with the following Reaction Scheme 1 [methods (aa), (bb) and (cc)]:

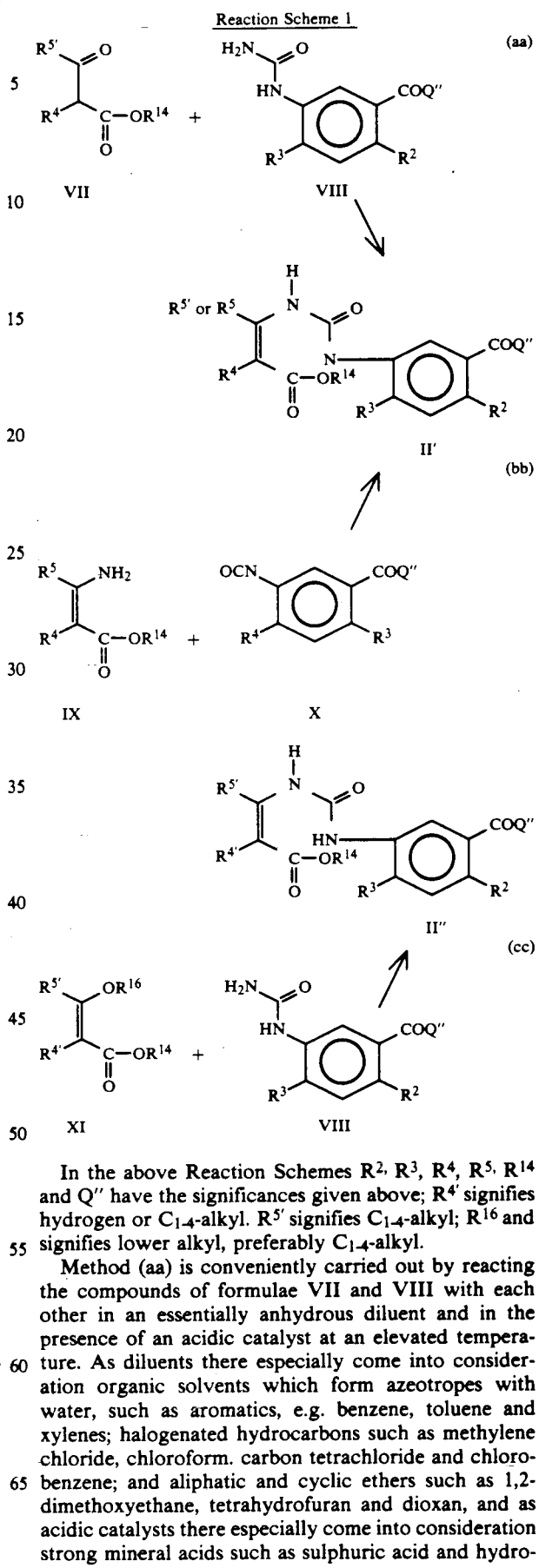

Reaction Scheme 1

In the above Reaction Schemes $R^2$, $R^3$, $R^4$, $R^5$, $R^{14}$ and Q″ have the significances given above; $R^{4'}$ signifies hydrogen or $C_{1-4}$-alkyl. $R^{5'}$ signifies $C_{1-4}$-alkyl; $R^{16}$ and signifies lower alkyl, preferably $C_{1-4}$-alkyl.

Method (aa) is conveniently carried out by reacting the compounds of formulae VII and VIII with each other in an essentially anhydrous diluent and in the presence of an acidic catalyst at an elevated temperature. As diluents there especially come into consideration organic solvents which form azeotropes with water, such as aromatics, e.g. benzene, toluene and xylenes; halogenated hydrocarbons such as methylene chloride, chloroform, carbon tetrachloride and chlorobenzene; and aliphatic and cyclic ethers such as 1,2-dimethoxyethane, tetrahydrofuran and dioxan, and as acidic catalysts there especially come into consideration strong mineral acids such as sulphuric acid and hydrochloric acid; organic acids such as p-toluenesulphonic acid; phosphorus-containing acids such as orthophosphoric acid and polyphosphoric acid; and acidic cation exchangers such as "Amberlyst 15" (Fluka). The reaction is generally carried out in a temperature range of about 70° C. to 120° C., preferably at the reflux temperature of the reaction mixture. Under these reaction conditions the desired rapid removal of the water which is formed in the reaction is achieved.

The reaction according to method bb) is conveniently effected in the presence of an essentially anhydrous aprotic organic solvent such as an aliphatic or cyclic ether, e.g. diethyl ether, 1,2-dimethoxyethane, tetrahydrofuran or dioxan, an aliphatic or aromatic hydrocarbon, e.g. n-hexane, benzene, toluene or a xylene; or a haloqenated. aliphatic hydrocarbon. e.q. methylene chloride, chloroform, carbon tetrachloride or 1,2-dichloroethane, as well as optionally in the presence of a base, especially an organic tertiary base such as triethylamine or pyridine, whereby the latter can serve not only as the solvent but also as the base, or a metal hydride such as sodium hydride or potassium hydride. The reaction temperatures are preferably in the range of about −80° C. to 50° C., with the reaction being carried out particularly at temperatures between −30° C. and room temperature.

The reaction according to method (cc) is conveniently carried out in an inert, water-miscible, organic solvent such as an aliphatic or cyclic ether, e.g. 1,2-dimethoxyethane, tetrahydrofuran or dioxan, or a lower alkanol such as ethanol at temperatures between 50° C. and 100° C., preferably at the reflux temperature of the reaction mixture, or in an aromatic solvent such as benzene, toluene or a xylene in the presence of an acidic catalyst such as hydrochloric acid or p-toluenesulphonic acid at temperatures between 50° C. and 100° C., preferably 60° C. to 80° C.

The starting materials of formulae III and V and their production are for the most part described in European patent publication No. 195,346. Those starting materials III and V whose production is not described can be produced analogously to the known starting materials. The reactive derivatives of the benzoic acids of formula III, which can likewise be used as starting materials, can be produced from these benzoic acids according to methods known per se. On the other hand, all enol ethers of the benzoic acids III, i.e. the compounds of general formulae IIIa and IIIb, which can likewise be used as starting materials in process variant (b), are novel. These can be produced. for example, in accordance with the following Reaction Scheme 2 in which $R^{1'}$, $R^2$, $R^3$, $R^4$, $R^5$, Hal and $M^\ominus$ have the significances given above and $R^{17}$ signifies lower alkyl, preferably $C_{1-4}$-alkyl:

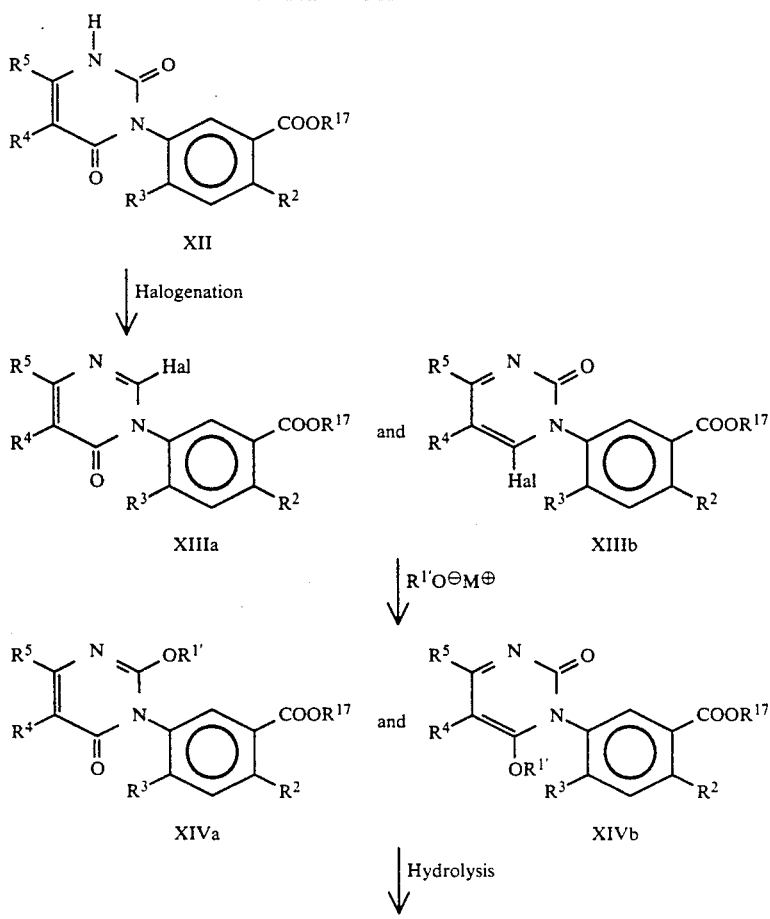

Reaction Scheme 2

-continued
Reaction Scheme 2

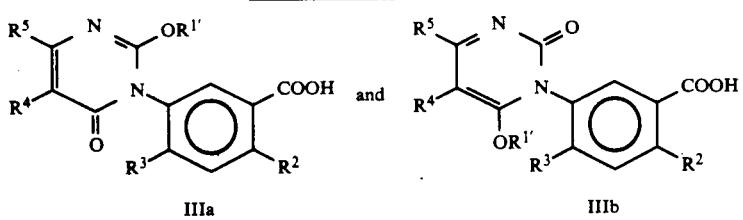

IIIa and IIIb

In the halogenation of the benzoic acid ester of formula XII there is used as the halogenating agent especially thionyl chloride phosphorus pentachloride or phosphorus oxychloride or phosphorus pentabromide or phosphoryl bromide. If desired, a mixture of phosphorus pentachloride and phosphorus oxychloride or of phosphorus pentabromide and phosphoryl bromide can be used, in which case an excess of phosphorus oxychloride or phosphoryl bromide can serve as the diluent. The chlorination or bromination can be carried out in the presence of an inert diluent, especially an aprotic organic solvent such as an aliphatic or aromatic hydrocarbon, e.g. n-hexane, benzene, toluene or a xylene; a halogenated aliphatic hydrocarbon, e.g. methylene chloride, chloroform or 1,2-dichloroethane; a halogenated aromatic hydrocarbon, e.g. chlorobenzene or a tertiary amine e.g. N,N-dimethylaniline, but this is not necessary when phosphorus oxychloride or phosphoryl bromide is used as the halogenating agent. When thionyl chloride is used as the halogenating agent it is has been found to be convenient to add a catalytic amount of dimethylformamide. The reaction temperatures generally lie between 0° C. and the reflux temperature of the reaction mixture, preferably between 80° C. and 120° C.

In this manner there is usually obtained a mixture of the two compounds XIIIa and XIIIb. If desired, such mixtures can be separated and the individual isomers can be subjected to the reaction with the metal alkanolate, alkenolate or alkynolate $R^1{}'O^\oplus M^\ominus$ or, preferably the isomer mixture XIIIa/XIIIb can be reacted with the metal alkanolate, alkenolate or alkynolate $R^{1''}O^\oplus M^\ominus$ and thereafter the product can be separated, if desired, into the individual compounds XIVa and XIVb. Such separations can be carried out according to methods known per se. The aforementioned product, namely the mixture of the two isomers XIVa and XIVb to be separated. is essentially in pure form, namely free from starting materials and different isomers. The reaction of the compound XIIIa or XIIIb or of the isomer mixture XIIIa/XIIIb with the metal alkanolate, alkenolate or alkynolate $R^1{}'O^\oplus M^\ominus$ can be effected analogously to the above-described process variant (d).

The subsequent hydrolysis of compound XIVa or XIVb can be carried out according to methods known per se, especially using an inorganic acid and optionally in the presence of an organic solvent and/or of water. As acids there preferably come into consideration hydrochloric acid, sulphuric acid and phosphoric acid, as organic solvents there preferably come into consideration alcohols, e.g. ethanol; aliphatic or cyclic ethers, e.g. 1,2-dimethoxyethane, tetrahydrofuran and dioxan, and optionally chlorinated aliphatic or alicyclic hydrocarbons, e.g. methylene chloride, carbon tetrachloride, n-hexane and cyclohexane. The reaction temperatures generally lie between $-20°$ C. and 120° C., preferably between 0° C. and 30° C., especially between 15° C. and 20° C.

The starting materials of formula VIa or VIb, which are used in process variant (d), can be produced by halogenating the corresponding uracil derivatives of the general formula

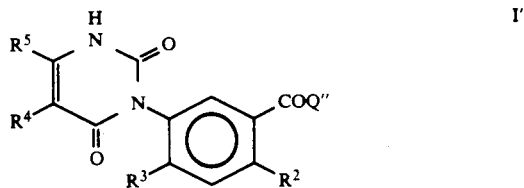

I'

Wherein $R^2$, $R^3$, $R^4$, $R^5$ and $Q''$ have the significances given above, analogously to the above-described process XII→XIIIa and XIIIb (see Reaction Scheme 2 and the description of the reaction conditions following therefrom). The uracil derivatives of formula I' are a sub-group of compounds of formula I which correspond to the products of process variant (a).

The remaining starting materials or reagents which are involved in process variants (b) to (d) as well as in the Reaction Schemes 1 and 2 are either known or can be produced according to methods known per se.

The compounds of formula I as well as their enol ethers and salts (referred to hereinafter together as compounds in accordance with the invention or active substances) possess herbicidal properties and are suitable for the control of weeds, including weed grasses, inter alia *Setaria faberii, Digitaria sanguinalis, Poa annua, Chenopodium album, Amaranthus retroflexus, Abutilon theophrasti, Sinapis arvensis* and *Datura stramonium*, in diverse crop cultivations, inter alia in cereal, soya, maize, rice and cotton cultivations. Moreover, the compounds are not only pre-emergence herbicides, but also post-emergence herbicides.

In practice, a concentration of 1 g to 3 kg of compound in accordance with the invention/ha, preferably 10 to 500 g of compound in accordance with the invention/ha, is sufficient to achieve the desired herbicidal effect.

The weed control composition in accordance with the invention is characterized in that it contains an effective amount of at least one compound of formula I, as defined above or of an enol ether or salt thereof as well as formulation adjuvants. The composition conveniently contains at least one of the following formulation adjuvants: solid carrier substances: solvents or dispersion media: tensides (wetting and emulsifying agents); dispersing agents (without tenside action); and stabilizers. With the use of these and other adjuvants these compounds, namely the herbicidally active substances, can be converted into the usual formulations such as dusts powders, granulates, solutions emulsions, suspensions, emulsifiable concentrates, pastes and the like.

The compounds of formula I and their enol ethers are generally insoluble in water, whereas the salts, especially the alkali metal salts and ammonium salts, are generally soluble in water, and can be formulated according to methods which are usual for water-insoluble or water-soluble compounds using the respective formulation adjuvants. The manufacture of the compositions can be carried out in a manner known per se, e.g. by mixing the respective active substance with solid carrier substances, by dissolution or suspension in suitable solvents or dispersion media, if necessary using tensides as wetting or emulsifying agents and/or dispersing agents, by diluting pre-prepared emulsifiable concentrates with solvents or dispersion media etc.

As solid carrier substances there essentially come into consideration: natural mineral substances such as chalk dolomite limestone aluminas and silicic acid and salts thereof (for example siliceous earth, kaolin, bentonite, talc, attapulgite and montmorillonite); synthetic mineral substances such as highly dispersible silicic acid, aluminium oxide and silicates; organic substances such as cellulose starch, urea and synthetic resins; and fertilizers such as phosphates and nitrates whereby such carrier substances can be present e g. as powders or as granulates.

As solvents or dispersion media there essentially come into consideration: aromatics such as benzene, toluene, xylenes and alkylnaphthalenes: chlorinated aromatics and chlorinated aliphatic hydrocarbons such as chlorobenzenes chloroethylenes and methylene chloride: aliphatic hydrocarbons such as cyclohexane and paraffins e.g. petroleum fractions; alcohols such as butanol and glycol, as well as their ethers and esters; ketones such as acetone, methyl ethyl ketone, methyl isobutyl ketone and cyclohexanone; and strongly polar solvents or dispersion media such as dimethylformamide N-methylpyrrolidone and dimethyl sulphoxide, such solvents preferably having flash points of at least 30° C. and boiling points of at least 50° C., and water. Among the solvents or dispersion media there also come into consideration so-called liquified gaseous extenders or carrier substances, which are those products which are gaseous at room temperature and under normal pressure. Examples of such products are especially aerosol propellants such as halogenated hydrocarbons. e.g. dichlorodifluoromethane. If the weed control composition in accordance with the invention is present in the form of a pressurized pack. then a solvent is conveniently used in addition to the propellant.

The tensides (wetting and emulsifying agents) can be non-ionic compounds such as condensation products of fatty acids, fatty alcohols or fatty-substituted phenols with ethylene oxide; fatty acid esters and ethers of sugars or polyvalent alcohols; the products which are obtained from sugars or polyvalent alcohols by condensation with ethylene oxide; block polymers of ethylene oxide and propylene oxide; or alkyldimethylamine oxides.

The tensides can also be anionic compounds such as soaps: fatty sulphate esters, e.g. dodecyl sodium sulphate, octadecyl sodium sulphate and cetyl sodium sulphate: alkyl sulphonates, aryl sulphonates and fattyaromatic sulphonates such as alkylbenzene sulphonates, e.g. calcium dodecylbenzenesulphonate, and butylnaphthalene sulphonates; and more complex fatty sulphonates, e.g. the amide condensation products of oleic acid and N-methyltaurine and the sodium sulphonate of dioctyl succinate.

Finally, the tensides can be cationic compounds such as alkyldimethylbenzylammonium chlorides, dialkyldimethylammonium chlorides, alkyltrimethylammonium chlorides and ethoxylated quaternary ammonium chlorides.

As dispersing agents (without tenside action) there essentially come into consideration; lignin, sodium and ammonium salts of liqnin sulphonic acids, sodium salts of maleic anhydride-diisobutylene copolymers, sodium and ammonium salts of sulphonated polycondensation products of naphthalene and formaldehyde, and sulphite lyes.

As dispersing agents, which are especially suitable as thickening or anti-settling agents, there can be used e.g. methylcellulose, carboxymethylcellulose, hydroxyethylcellulose, polyvinyl alcohol, alginates, caseinates and blood albumin.

Examples of suitable stabilizers are acid-binding agents. e.g. epichlorohydrin, phenyl glycidyl ether and soya epoxides; antioxidants. e.g. gallic acid esters and butylhydroxytoluene: UV-absorbers, e.g. substituted benzophenones, diphenylacrylonitrile acid esters and cinnamic acid esters; and deactivators, e.g. salts of ethylenediaminotetraacetic acid and polyglycols. The weed control compositions in accordance with the invention can contain, in addition to the active substances in accordance with the invention, synergists and other active substances, e.g. insecticides, acaricides, fungicides, plant growth regulators and fertilizers. Such combination compositions are suitable for intensifyinq the activity or for broadening the spectrum of activity.

The weed control compositions in accordance with the invention generally contain between 0.001 and 95 weight percent, preferably between 0.5 and 75 weight percent, of one or more compounds in accordance with the invention as the active substance(s). They can be present e.g. in a form which is suitable for storage and transport. In such formulations, e.g. emulsifiable concentrates, the active substance concentration is normally in the higher range, preferably between 1 and 50 weight percent, especially between 5 and 30 weight percent. These formulations can then be diluted, e.g. with the same or different inert substances, to give active substance concentrations which are suitable for practical use, i.e. preferably about 0.001 to 10 weight percent, especially about 0.005 to 5 weight percent. The active substance concentrations can, however, also be smaller or greater.

As mentioned above, the manufacture of the weed control compositions in accordance with the invention can be carried out in a manner known per se.

For the manufacture of pulverous preparations the active substance, i.e. at least one compound in accordance with the invention, can be mixed with a solid carrier substance e.g. by grinding together; or the solid carrier substance can be impregnated with a solution or suspension of the active substance and then the solvent or dispersion off under reduced pressure. By adding tensides or dispersing agents such pulverous preparations can be made readily wettable with water. so that they can be converted into aqueous suspensions which are suitable e.g. as spray compositions.

The active substance can also be mixed with a tenside and a solid carrier substance to form a wettable powder which is dispersible in water or it can be mixed with a solid pre-granulated carrier substance to form a product in the form of a granulate.

When desired, the active substance can be dissolved in a water-immiscible solvent such as for example, a high-boiling hydrocarbon, which conveniently contains dissolved emulsifying agent, so that the solution becomes self-emulsifying upon addition to water. Alternatively the active substance can be mixed with an emulsifying agent and the mixture can then be diluted with water to the desired concentration. Moreover, the active substance can be dissolved in a solvent and thereafter the solution can be mixed with an emulsifying agent. Such a mixture can likewise be diluted with water to the desired concentration. In this manner there are obtained emulsifiable concentrates or ready-for-use emulsions.

The use of the weed control compositions in accordance with the invention, which forms a further object of the present invention, can be carried out according to usual application methods such as sprinkling, spraying, dusting, watering or scattering. The method in accordance with the invention for the control of weeds is characterized by treating the locus to be protected against weeds and/or the weeds with a compound in accordance with the invention or with a weed control composition in accordance with the invention.

The following Examples serve to illustrate the invention in more detail.

I. Manufacture of the compounds of formula I and, respectively, of their enol ethers

EXAMPLE 1

0.9 g of 3-pentanone oxime is added at room temperature to a suspension of 3.0 g of 2-chloro-5-[3,6-dihydro-2,6-dioxo-3-methyl-4-trifluoromethyl-1(2H)-pyrimidinyl]-4-fluorobenzoic acid in 50 ml of diethyl ether. Thereafter, a solution of 1.9 g of dicyclohexylcarbodiimide and 0.1 g of 4-pyrrolidinopyridine in 15 ml of diethyl ether is added dropwise over 10 minutes. The reaction mixture is stirred at room temperature for 12 hours. Subsequently, it is filtered and evaporated to dryness under reduced pressure. The residue is purified by chromatography on silica gel with n-hexane/diethyl ether (4:1) as the eluent. In this manner there is obtained 3-pentanone O-{2-chloro-5-[3,6-dihydro-2,6-dioxo-3-methyl-4 -trifluoromethyl-1(2H)-pyrimidinyl]-4-fluorobenzoyl}oxime, m.p. 128°-130° C.

Examples 2-11

The compounds of formula I set forth in Table 1 hereinafter are obtained analogously to the procedure described in Example 1 starting from 2-chloro-5-[3,6-dihydro-2,6-dioxo-3-methyl-4-trifluoromethyl-1(2H)-pyrimidinyl]-4-fluorobenzoic acid and the corresponding hydroxy compound of the formula H-Q:

TABLE 1

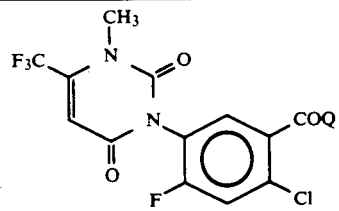

| Example | Q | Physical data |
|---|---|---|
| 2 | O—N=C(CH$_3$)(—◁) | M.p. 146–148° C. |
| 3 | O—N=C(isoC$_3$H$_7$)$_2$ | M.p. 113–115° C. |
| 4 | O—N=C(CH$_3$)(isoC$_3$H$_7$) | M.p. 50–52° C. |
| 5 | O—(CH$_2$)$_2$—ON=C(CH$_3$)(C$_2$H$_5$) | $^1$H-NMR (CDCl$_3$, 60 MHz): 7.98 ppm (d,1H), 7.42 ppm (d,1H), 6.43 ppm (s,1H), 4.51 ppm (m,4H), 3.62 ppm (d,4H), 2.26 ppm (q,2H), 1.91 ppm (s,3H), 1.20 ppm (m,6H) |
| 6 | O—(CH$_2$)$_2$—ON=⬡ | $^1$H-NMR (CDCl$_3$, 60 MHz): 7.99 ppm (d,1H), 7.41 ppm (d,1H), 6.43 ppm (s,1H), 5.50 ppm (m,1H), 4.24 ppm (d,2H), 3.65 ppm (s,3H), 1.91 ppm (s,6H), 1.42 ppm (d,3H) |
| 7 | O—CH(CH$_3$)CH$_2$—ON=C(CH$_3$)$_2$ | $^1$H-NMR (CDCl$_3$, 60 MHz): 7.96 ppm (d,1H), 7.43 ppm (d,1H), 6.43 ppm (s,1H), 5.50 ppm (m,1H), 4.24 ppm (d,2H), 3.65 ppm (s,3H), 1.91 ppm (s,6H), 1.42 ppm (d,3H) |
| 8 | O—N=⬡ | M.p. 120–122° C. |
| 9 | O—CH(C$_2$H$_5$)CH$_2$—ON=C(CH$_3$)$_2$ | $^1$H-NMR (CDCl$_3$, 60 MHz): 7.89 ppm (d,1H), 7.40 ppm (d,1H), 6.36 ppm (s,1H), 5.34 ppm (m,1H), 4.22 ppm (d,2H), 3.58 ppm (s,3H), 1.30 ppm (m,11H) |
| 10 | O—CH(C$_6$H$_5$)CH$_2$—ON=C(CH$_3$)$_2$ | M.p. 50–51° C. |
| 11 | O—N=C(CH$_3$)(OC$_2$H$_5$) | $^1$H-NMR (CDCl$_3$, 60 MHz): 7.92 ppm (d,1H), 7.46 ppm (d,1H), 6.40 ppm (s,1H), 4.32 ppm (q,2H), 3.60 ppm (d,3H), 2.18 ppm (s,3H), 1.39 ppm (t,3H) |

EXAMPLES 12-14

The compounds of formula I set forth in Table 2 hereinafter are obtained analogously to the procedure described in Example 1 starting from 2-chloro-5-[3,6-dihydro-2,6-dioxo-3-methyl or difluoromethyl-4-methyl-1(2H)-pyrimidinyl]-4-fluorobenzoic acid and the corresponding hydroxy compound of the formula H-Q:

TABLE 2

Structure: pyrimidinedione with R¹ on N, H₃C group, linked via N to fluoro-chloro-benzoate (COQ)

| Example | R¹ | Q | Physical data |
|---|---|---|---|
| 12 | CH₃ | O—N=C(CH₃)₂ | ¹H-NMR (CDCl₃, 60 MHz): 7.90 ppm (d,1H), 7.43 ppm (d,1H), 5.79 ppm (s,1H), 3.50 ppm (s,3H), 2.37 ppm (s,3H), 2.14 ppm (s,6H). |
| 13 | CH₃ | O—(CH₂)₂—ON=C(CH₃)₂ | ¹H-NMR (CDCl₃, 60 MHz): 7.91 ppm (d,1H), 7.36 ppm (d,1H), 5.76 ppm (s,1H), 4.43 ppm (m,4H), 3.48 ppm (s,3H), 2.35 ppm (s,3H), 1.88 ppm (s,6H). |
| 14 | CHF₂ | O—(CH₂)₂—ON=C(CH₃)₂ | ¹H-NMR (CDCl₃, 60 MHz): 7.90 ppm (d,1H), 7.79 ppm (t,1H), 7.40 ppm (d,1H), 5.88 ppm (s,1H), 4.45 ppm (m,4H), 2.54 ppm (m,3H), 1.89 ppm (s,6H). |

EXAMPLE 15

A mixture of 1.5 g of 2-chloro-4-fluoro-5-[2methoxy-6-oxo-4-trifluoromethyl-1(6H)-pyrimidinyl]-benzoic acid, 1.37 g of 1,1,3-tribromo-1-propene and 0.52 g of sodium carbonate in 50 ml of anhydrous acetone is heated for 8 hours while stirring. Subsequently, the insoluble constituents are filtered off under suction and the filtrate is evaporated to dryness under reduced pressure. The residue is dissolved in 100 ml of diethyl ether and the solution is extracted three times with 50 ml of water each time. The organic phase is then dried over anhydrous sodium sulphate and evaporated to dryness, and the residue is purified by chromatography on a silica gel column using n-hexane/diethyl ether (3:1) as the eluent. There is obtained 3,3-dibromo-2-propenyl 2-chloro-4-fluoro-5-[2-methoxy-6-oxo-4-trifluoromethyl-1(6H)-pyrimidinyl]benzoate, ¹H-NMR (CDCl₃, 400 MHz): 7.89 ppm (d, 1H), 7.42 ppm (d, 1H), 6.72 ppm (t, 1H), 6.62 ppm (s. 1H), 4.82 ppm (d, 2H), 4.02 ppm (d, 3H).

Alternatively, this process can be carried out for example, using sodium hydride as the base and dimethylformamide as the solvent.

EXAMPLE 16-26

The compounds of formula I and enol ethers set forth in Tables 3 and 4 are obtained analogously to the procedure described in Example 15 starting from 2-chloro-4-fluoro-5-[2-methoxy-6-oxo-4-trifluoromethyl-1(6H)-pyrimidinyl]-benzoic acid and, respectively, 2-chloro-5-[3,6-dihydro-2,6-dioxo-3-methyl-4-trifluoro-methyl-1(2H)-pyrimidinyl]-4-fluorobenzoic acid and the corresponding halide (reactive derivative of the hydroxy compound H-Q):

TABLE 3

Structure: pyrimidine with F₃C and OCH₃ groups, linked via N to fluoro-chloro-benzoate (COQ')

| Example | Q' | Physical data |
|---|---|---|
| 16 | O—CH₂CH=CCl₂ | ¹H-NMR (CDCl₃, 400 MHz): 7.88 ppm (d,1H), 7.42 ppm (d,1H), 6.63 ppm (s,1H), 6.17 ppm (t,1H), 4.92 ppm (d,2H), 4.02 ppm (d,3H) |
| 17 | O—CH₂CH=C(Cl)(CH₃) (E/Z) | ¹H-NMR (CDCl₃, 400 MHz): 7.87 ppm (2d,1H), 7.41 ppm (2d,1H), 6.62 ppm (2s,1H), 5.92-5.74 ppm (m,1H), 4.98-4.76 ppm (m,2H), 4.02 ppm (2s,3H), 2.24-2.14 ppm (m,3H) |
| 18 | O—CH₂CH=CHCH₂Cl (E/Z) | ¹H-NMR (CDCl₃, 400 MHz): 7.88 ppm (2d,1H), 7.42 ppm (2d,1H), 6.62 ppm (2s,1H), 6.04-5.80 ppm (m,2H), 4.96-4.82 ppm (m,2H), 4.22-4.06 ppm (m,2H), 4.02 ppm (2s,3H) |
| 19 | O—CH₂C=CCH₂Br | M.p. 113-115° C. |

TABLE 4

Structure: pyrimidinedione with CH₃ on N and F₃C group, linked via N to fluoro-chloro-benzoate (COQ)

| Example | Q | Physical data |
|---|---|---|
| 20 | O—CH₂CH=CBr₂ | ¹H-NMR (CDCl₃, 400 MHz): 7.92 ppm (d,1H), 7.40 ppm (d,1H), 6.71 ppm (t,1H), 6.38 ppm (s,1H), 4.81 ppm (d,2H), 3.57 ppm (m,3H) |
| 21 | O—CH₂CH=CCl₂ | ¹H-NMR (CDCl₃, 400 MHz): 7.91 ppm (d,1H), 7.40 ppm (d,1H), 6.38 ppm (s,1H), 6.16 ppm (t,1H), 4.90 ppm (d,2H), 3.57 ppm (m,3H) |
| 22 | O—CH₂CH=C(Cl)(CH₃) (E/Z) | ¹H-NMR (CDCl₃, 400 MHz): 7.90 ppm (2d,1H), 7.39 ppm (2d,1H), 6.37 ppm (2s,1H), 5.72-5.92 ppm (2m,1H), 4.76-4.98 ppm (m,2H), 3.56 ppm (m,3H), |

TABLE 4-continued

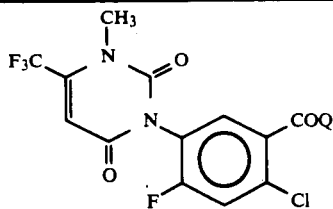

| Example | Q | Physical data |
|---|---|---|
| 23 | O—CH$_2$CH=CHCH$_2$Cl (E/Z) | 2.18 ppm (m,3H) $^1$H-NMR (CDCl$_3$, 400 MHz): 7.89 ppm (2d,1H), 7.39 ppm (2d,1H), 6.37 ppm (2s,1H), 6.02–5.80 ppm (m,2H), 4.96–4.80 ppm (m,2H), 4.22–4.04 ppm (m,2H), 3.56 ppm (m,3H) |
| 24 | O—CH$_2$C≡CCH$_2$Br | $^1$H-NMR (CDCl$_3$, 400 MHz): 7.95 ppm (d,1H), 7.40 ppm (d,1H), 6.38 ppm (s,1H), 4.97 ppm (t,2H), 3.94 ppm (t,2H), 3.57 ppm (t,3H) |
| 25 | O—CH$_2$C≡CCl | $^1$H-NMR (CDCl$_3$, 400 MHz): 7.94 ppm (d,1H), 7.40 ppm (d,1H), 6.38 ppm (s,1H), 4.89 ppm (s,2H), 3.56 ppm (m,3H) |
| 26 | O—CH$_2$CH=CHCl (E/Z) | $^1$H-NMR (CDCl$_3$, 400 MHz): 7.90 ppm (2d,1H), 7.39 ppm (2d,1H), 6.43 and 6.29 ppm (2m,1H), 6.37 ppm (2s,1H), 6.13 and 6.04 ppm (2m,1H), 5.02 and 4.79 ppm (2q,2H), 3.56 ppm (2m,3H) |

EXAMPLES 27–31

The compounds of formula I set forth in Table 5 hereinafter are obtained analogously to the procedure described in Example 15 starting from the corresponding 2-chloro-5[3,6-dihydro-2,6-dioxo-3,4-disubstituted-1(2H)-pyrimidinyl]-4-fluorobenzoic acid and the corresponding hydroxy compound of the formula H-Q:

TABLE 5

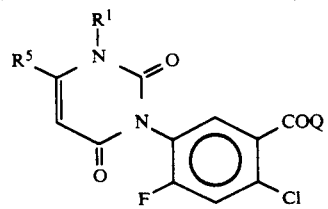

| Example | R$^1$ | Q | R$^5$ | Physical data |
|---|---|---|---|---|
| 27 | CH$_3$ | O—CH$_2$C(Cl)=CH$_2$ | C$_2$F$_5$ | $^1$H-NMR (CDCl$_3$, 400 MHz): 7.95 ppm (d,1H), 7.41 ppm (d,1H), 6.33 ppm (s,1H), 5.57 ppm (m,1H), 5.47 ppm (d,1H), 4.89 ppm (d,2H), 3.57 ppm (m,3H) |
| 28 | CH$_3$ | O—CH$_2$C≡CCl | CH$_3$ | $^1$H-NMR (CDCl$_3$, 60 MHz): 7.91 ppm (d,1H), 7.36 ppm (d,1H), 5.74 ppm (s,1H), 4.89 ppm (s,2H), 3.45 ppm (s,3H), 2.32 ppm (s,3H) |
| 29 | CH$_3$ | O—CH$_2$—CH=CCl$_2$ | CH$_3$ | M.p. 131–133° C. |
| 30 | CH$_3$ | O—CH$_2$CH$_2$Cl | CH$_3$ | $^1$H-NMR (CDCl$_3$, 60 MHz): 7.92 ppm (d,1H), 7.36 ppm (d,1H), 5.74 ppm (s,1H), 4.55 ppm (t,2H), 3.78 ppm (t,2H), 3.45 ppm (s,3H), 2.32 ppm (s,3H) |
| 31 | CHF$_2$ | O—CH$_2$CH$_2$Cl | CH$_3$ | $^1$H-NMR (CDCl$_3$, 60 MHz): 7.92 ppm (d,1H), 7.72 ppm (t,1H), 7.39 ppm (d,1H), 5.84 ppm (s,1H), 4.57 ppm (t,2H), 3.78 ppm (t,2H), 2.50 ppm (s,3H) |

EXAMPLE 32

2.5 g of 2-chloro-5[3,6-dihydro-2,6-dioxo-3-methyl-4-trifluoromethyl-1(2H)-pyrimidinyl]-4fluorobenzoic acid are heated at reflux temperature for 3 hours in 20 ml of benzene and 2.4 ml of thionyl chloride together with one drop of dimethylformamide. Subsequently, the reaction mixture is evaporated to dryness and dissolved in 15 ml of dioxan. This solution, which consists mainly of the acid chloride of the above-mentioned benzoic acid and the solvent, is added dropwise at room temperature to a solution of 0.7 g of isopropyl mercaptan and 0.8 g of pyridine in 10 ml of dioxan. The reaction mixture is then stirred at room temperature for 2.5 hours, treated with 300 ml of water and extracted twice with 300 ml of ethyl acetate each time. The combined organic phases are washed twice with 150 ml of 1N hydrochloric acid each time and once with 150 ml of saturated sodium chloride solution, dried over anhydrous sodium sulphate and evaporated. The residue is purified by chromatography on silica gel with ethyl acetate/n-hexane (2:3). In this manner there is obtained S-isopropyl 2-chloro-5-[3,6-dihydro-2 6-dioxo-3-methyl-4 -trifluoromethyl-1(2H)-pyrimidinyl]-4-fluorothiobenzoate as a viscous oil.

Mass spectrum (m/e): $M^+ 424$ (0.6); $^1$H-NMR (CDCl$_3$, 400 MHz): 7.96 ppm (d,1H). 7.91 ppm (d,1H), 6.61 ppm (s,1H), 3.78 ppm (septet.1H). 3.42 ppm (s,3H). 1.36 ppm (d,6H).

Alternatively. this process can be carried out using, for example, methylene chloride as the solvent.

EXAMPLE 33-60

The compounds of formula I set forth in Table 6 hereinafter are obtained analogously to the procedure described in Example 32 starting from 2-chloro-5-[3,6-dihydro-2,6-dioxo-3-methyl-4-substituted-1(2H)-pyrimidinyl]-4-fluorobenzoic acid via its acid chloride and the corresponding hydroxy or mercapto compound H-Q:

TABLE 6

| Example | $R^5$ | Q | Physical data |
|---|---|---|---|
| 33 | CF$_3$ | O—N=C(CH$_3$)$_2$ | $^1$H-NMR (CDCl$_3$, 400 MHz):<br>7.87 ppm (d,1H), 7.40 ppm (d,1H), 6.37 ppm (s,1H),<br>3.56 ppm (m,3H), 2.11 ppm (s,3H), 2.13 ppm (s,3H) |
| 34 | CF$_3$ | 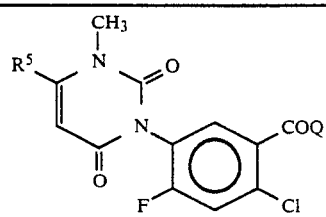 O—N=C(CH$_3$)(—⟨furan⟩) | M.p. 73–75° C. |
| 35 | CF$_3$ | O—N=C(CH$_3$)(COOCH$_3$) | $^1$H-NMR (CDCl$_3$, 60 MHz):<br>7.96 ppm (d,1H), 7.50 ppm (d,1H), 6.44 ppm (s,1H),<br>3.61 ppm (s,3H), 2.60 ppm (s,3H), 2.20 ppm (s,3H) |
| 36 | CF$_3$ | O—(CH$_2$)$_2$—ON=C(CH$_3$)$_2$ | $^1$H-NMR (CDCl$_3$, 250 MHz):<br>7.92 ppm (d,1H), 7.39 ppm (d,1H), 6.38 ppm (s,1H),<br>4.53 ppm (m,2H), 4.31 ppm (m,2H), 3.57 ppm (m,1H),<br>1.85 ppm (s,3H), 1.84 ppm (s,3H) |
| 37 | CF$_3$ | O—CH$_2$CH$_2$Cl | $^1$H-NMR (CDCl$_3$, 400 MHz):<br>7.93 ppm (d,1H), 7.41 ppm (d,1H), 6.38 ppm (s,1H),<br>4.57 ppm (m,2H), 3.80 ppm (m,2H), 3.57 ppm (m,3H) |
| 38 | CF$_3$ | O—CH$_2$CH$_2$F | $^1$H-NMR (CDCl$_3$, 400 MHz):<br>7.95 ppm (d,1H), 7.41 ppm (d,1H), 6.38 ppm (s,1H),<br>4.71 ppm (m,2H), 4.56 ppm (m,2H), 3.57 ppm (m,3H) |
| 39 | CF$_3$ | O—CH$_2$CH$_2$Br | $^1$H-NMR (CDCl$_3$, 400 MHz):<br>7.94 ppm (d,1H), 7.41 ppm (d,1H), 6.38 ppm (s,1H),<br>4.63 ppm (t,2H), 3.63 ppm (t,2H), 3.58 ppm (m,3H) |
| 40 | CF$_3$ | O—CH(CH$_2$Cl)$_2$ | $^1$H-NMR (CDCl$_3$, 400 MHz):<br>7.91 ppm (d,1H), 7.42 ppm (d,1H), 6.39 ppm (s,1H),<br>5.42 ppm (m,1H), 3.87 ppm (q,4H), 3.57 ppm (m,3H) |
| 41 | CF$_3$ | O—CH(CH$_2$F)$_2$ | $^1$H-NMR (CDCl$_3$, 400 MHz):<br>7.93 ppm (d,1H), 7.42 ppm (d,1H), 6.38 ppm (s,1H),<br>5.45 ppm (m,1H), 4.71 ppm (m,4H), 3.57 ppm (m,3H) |
| 42 | CF$_3$ | S—CH$_2$C$_6$H$_5$ | Oil;<br>mass spectrum (m/e): $M^+$ 472 (4.4);<br>$^1$H-NMR(D$_6$-DMSO, 400 MHz):<br>7.98 ppm (d,1H), 7.93 ppm (d,1H), 7.41–7.25 ppm (m,5H), 6.60 ppm (s,1H), 4.37 ppm (s,2H), 3.40 ppm (s,3H) |
| 43 | CF$_3$ | S—C$_4$H$_9$n | M.p. 83–84° C. |
| 44 | CF$_3$ | S—C$_2$H$_5$ | M.p. 88–89° C. |
| 45 | CF$_3$ | S—CH$_2$CH=CH$_2$ | Oil;<br>mass spectrum (m/e): $M^+$ 422 (1.1);<br>$^1$H-NMR(D$_6$-DMSO, 400 MHz):<br>8.00 ppm (d,1H), 7.92 ppm (d,1H), 6.61 ppm (s,1H), 5.94–5.72 ppm (m,1H), 5.35 ppm (m,1H), 5.17 ppm (m,1H), 3.77 ppm (m,2H), 3.42 ppm (s,3H) |

TABLE 6-continued

[Structure: pyrimidine-2,4-dione with N-CH3, R5 substituent, linked via N to a benzene ring bearing COQ, F, and Cl substituents]

| Example | R⁵ | Q | Physical data |
|---|---|---|---|
| 46 | CF₃ | S—cyclohexyl | Oil; ¹H-NMR (D₆-DMSO, 400 MHz): 7.96 ppm (d,1H), 7.90 ppm (d,1H), 6.61 ppm (s,1H), 3.73–3.62 ppm (m,1H), 3.42 ppm (s,3H), 2.00–1.90 ppm (m,2H), 1.72–1.38 ppm (m,7H), 1.36–1.24 ppm (m,1H); Microanalysis: C% H% N% S% Cl% Calculated 49.09 3.69 6.03 6.90 7.63 Found 49.09 3.62 5.79 7.08 7.55 |
| 47 | CF₃ | S—phenyl | M.p. 153–154° C. |
| 48 | CF₃ | O—CH₂CF₃ | ¹H-NMR (CDCl₃, 400 MHz): 7.94 ppm (d,1H), 7.43 ppm (d,1H), 6.38 ppm (s,1H), 4.68 ppm (m,2H), 3.57 ppm (m,3H) |
| 49 | CF₃ | O—CH(CF₃)₂ | ¹H-NMR (CDCl₃, 400 MHz): 7.96 ppm (d,1H), 7.47 ppm (d,1H), 6.39 ppm (s,1H), 5.99 ppm (m,1H), 3.57 ppm (m,3H) |
| 50 | CF₃ | O—N=C(CH₂COOC₂H₅)₂ | ¹H-NMR (CDCl₃, 60 MHz): 7.95 ppm (d,1H), 7.46 ppm (d,1H), 6.41 ppm (s,1H), 4.22 ppm (m,4H), 3.79 ppm (m,4H), 1.78 ppm (m,6H) |
| 51 | CF₃ | O—N=C(CH₃)(CH₂COOC₂H₅) | ¹H-NMR (CDCl₃, 60 MHz): 7.94 ppm (d,1H), 7.48 ppm (d,1H), 6.42 ppm (s,1H), 4.24 ppm (q,2H), 3.60 ppm (m,3H), 3.41 ppm (s,2H), 2.25 ppm (s,3H), 1.30 ppm (t,3H) |
| 52 | CF₃ | O—N=C(CH₃)(C₆H₅) | ¹H-NMR (CDCl₃, 60 MHz): 7.91 ppm (d,1H), 7.58 ppm (m,5H), 7.45 ppm (d,1H), 6.40 ppm (s,1H), 3.64 ppm (m,3H), 2.53 ppm (s,3H) |
| 53 | CF₃ | O—N=C(CH₃)(COCH₃) | ¹H-NMR (CDCl₃, 60 MHz): 7.96 ppm (d,1H), 7.50 ppm (d,1H), 6.44 ppm (s,1H), 3.61 ppm (m,3H), 2.60 ppm (s,3H), 2.20 ppm (s,3H) |
| 54 | CF₃ | O—N=C(CH₃)(COOC₂H₅) | ¹H-NMR (CDCl₃, 60 MHz): 7.96 ppm (d,1H), 7.50 ppm (d,1H), 6.43 ppm (s,1H), 4.46 ppm (q,2H), 3.65 ppm (m,3H), 2.39 ppm (s,3H), 1.47 ppm (t,3H) |
| 55 | CF₃ | O—N=C(CH₃)(CH₂OCH₃) | ¹H-NMR (CDCl₃, 60 MHz): 7.93 ppm (d,1H), 7.49 ppm (d,1H), 6.41 ppm (s,1H), 4.24 ppm (m,2H), 3.61 ppm (m,3H), 3.45 ppm (s,3H), 2.25 ppm (s,3H) |
| 56 | CF₃ | O—N=C(CH₃)(CF₃) | ¹H-NMR (CDCl₃, 60 MHz): 7.90 ppm (d,1H), 7.45 ppm (d,1H), 6.40 ppm (s,1H), 3.62 ppm (m,3H), 2.35 ppm (s,3H) |
| 57 | C₂F₅ | O—CH₂CF₃ | ¹H-NMR (CDCl₃, 400 MHz): 7.95 ppm (d,1H), 7.44 ppm (d,1H), 6.34 ppm (s,1H), 4.69 ppm (m,2H), 3.58 ppm (m,3H) |
| 58 | C₂F₅ | O—(CH₂)₄Cl | ¹H-NMR (CDCl₃, 400 MHz): 7.89 ppm (d,1H), 7.39 ppm (d,1H), 6.33 ppm (s,1H), 4.36 ppm (m,2H), 3.58 ppm (m,5H), 1.93 ppm (m,4H) |
| 59 | C₂F₅ | O—CH(CF₃)₂ | ¹H-NMR (CDCl₃, 400 MHz): 7.96 ppm (d,1H), 7.48 ppm (d,1H), 6.35 ppm (s,1H), 5.99 ppm (m,1H), 3.59 ppm (m,3H) |
| 60 | CH₃ | S—CH(CH₃)₂ | ¹H-NMR (D₆-DMSO, 400 MHz): 7.86–7.83 ppm (m,2H), 5.80 ppm (s,1H), 3.76 ppm (septet,1H), 3.35 ppm (s,3H), 2.33 ppm (s,3H), 1.36 ppm (d,6H) mass spectrum (m/e): M⁺ 370(2) |

EXAMPLES 61–66

The enol ethers of the compounds of formula I set forth in Table 7 hereinafter are obtained analogously to the procedure described in Example 32 starting from 2-chloro-4-fluoro-5-[2-methoxy-6-oxo-4-trifluoromethyl or pentafluoroethyl-1(6H)-pyrimidinyl]-benzoic acid via its acid chloride and the corresponding hydroxy compound H-Q':

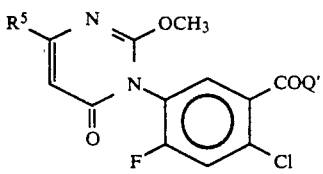

TABLE 7

R⁵, Q', Physical data structure shown above table.

| Example | R⁵ | Q' | Physical data |
|---|---|---|---|
| 61 | CF₃ | O—CH₂CH₂Cl | ¹H-NMR (CDCl₃,400 MHz): 7.91 ppm (d,1H), 7.43 ppm (d,1H), 6.63 ppm (s,1H), 4.59 ppm (m,2H), 4.03 ppm (s,3H), 3.81 ppm (t,2H) |
| 62 | CF₃ | O—CH(CH₂F)₂ | ¹H-NMR (CDCl₃,400 MHz): 7.90 ppm (d,1H), 7.44 ppm (d,1H), 6.63 ppm (s,1H), 5.47 ppm (m,1H), 4.73 ppm (m,4H), 4.03 ppm (s,3H) |
| 63 | CF₃ | O—(CH₂)₂—O—N=C(CH₃)₂ | ¹H-NMR (CDCl₃, 400 MHz): 7.89 ppm (d,1H), 7.40 ppm (d,1H), 6.62 ppm (s,1H), 4.56 ppm (m,2H), 4.32 ppm (m,2H), 4.02 ppm (s,3H), 1.85 ppm (s,3H), 1.84 ppm (s,3H) |
| 64 | C₂F₅ | O—CH₂CF₃ | ¹H-NMR (CDCl₃, 400 MHz): 7.93 ppm (d,1H), 7.46 ppm (d,1H), 6.68 ppm (s,1H), 4.71 ppm (m,2H), 4.01 ppm (s,3H) |
| 65 | C₂F₅ | O—(CH₂)₅Cl | ¹H-NMR (CDCl₃, 400 MHz): 7.86 ppm (d,1H), 7.41 ppm (d,1H), 6.67 ppm (s,1H), 4.35 ppm (t,2H), 3.99 ppm (s,3H), 3.56 ppm (t,2H), 1.82 ppm (m,4H), 1.61 ppm (m,2H) |
| 66 | C₂F₅ | O—CH(CF₃)₂ | ¹H-NMR (CDCl₃, 400 MHz): 7.95 ppm (d,1H), 7.50 ppm (d,1H), 6.69 ppm (s,1H), 6.00 ppm (m,1H), 4.02 ppm (s,3H) |

II. production of the starting materials of formulae III and IIIa

EXAMPLE 67

The 2-chloro-4-fluoro-5-[2-methoxy-6-oxo-4-trifluoro-methyl-1(6H)-pyrimidinyl]-benzoic acid used as the starting material in Examples 15–19 and 61–63 can be produced as follows:

A solution of 3.55 g of ethyl 3-amino-4,4,4-trifluorocrotonate in 50 ml of n-hexane is added dropwise while stirring at 0°–3° C. during 15 minutes to 0.85 g of a 55% sodium hydride dispersion in 50 ml of dimethylformamide and the mixture is stirred for 30 minutes. Subsequently, a solution of 5.0 g of isopropyl 2-chloro-4-fluoro-5-isocyanatobenzoate in 100 ml of n-hexane is added dropwise during 5 minutes while stirring and cooling. The temperature of the reaction mixture rises to 10° C. and the mixture is thereafter stirred at room temperature for one hour. The intermediate, isopropyl 2-chloro-4-fluoro-5-{3-[2-(ethoxycarbonyl)-1-trifluoromethyl-vinyl]ureido}benzoate, which thereby precipitates, is not isolated.

The mixture is brought to pH 4 by adding concentrated acetic acid, poured into 750 ml of water and the aqueous mixture is extracted with 300 ml of ethyl acetate. The organic phase is dried over anhydrous sodium sulphate and subsequently evaporated to dryness under reduced pressure and the residue is recrystallized from diethyl ether/n-hexane. In this manner there is obtained isopropyl 2-chloro-5-[3,6-dihydro-4-trifluoromethyl-2,6-dioxo-1(2H)-pyrimidinyl]-4-fluorobenzoate, m.p. 127°–129° C.

23.3 g of pyridine are added at room temperature while stirring and cooling to a suspension of 38.8 g of isopropyl 2-chloro-5-[3,6-dihydro-2,6-dioxo-4-trifluoromethyl-1(2H)-pyrimidinyl]-4-fluorobenzoate in 45.2 g of phosphorus oxychloride and 40 ml of toluene. A solution forms rapidly. The temperature is held between 30° to 35° C. and, after 15 minutes, a colourless precipitate begins to separate. The reaction mixture is stirred at 30°–35° C. for 45 minutes and is then poured onto 300 g of ice. Subsequently, the mixture is extracted with 200 ml of ethyl acetate and the organic phase is washed three times with 50 ml of water each time, dried over anhydrous sodium sulphate and evaporated to dryness under reduced pressure. The residue is recrystallized from n-hexane. There is obtained isopropyl 2-chloro-5-[2-chloro-6-oxo-4-trifluoro-methyl-1(6H)-pyrimidinyl]-4-fluorobenzoate, m.p. 72°–75° C.

51.3 ml of a 2N solution of sodium methylate in methanol are added dropwise while stirring and cooling at 0° C. during 5 minutes to a solution of 42.4 g of isopropyl 2-chloro-5-[2-chloro-6-oxo-4-trifluoromethyl-1(6H)-pyrimidinyl]-4-fluorobenzoate in 100 ml of absolute methanol. The reaction mixture is stirred at 0° C. for 10 minutes and adjusted to about pH 4 with concentrated acetic acid. Subsequently, the reaction mixture is evaporated to dryness under reduced pressure. The residue is dissolved in 300 ml of diethyl ether and the solution is washed twice with 100 ml of water each time. The organic phase is dried over anhydrous sodium sulphate and evaporated to dryness. The residue is purified by chromatography on a silica gel column using n-hexane/diethyl ether (3:1) as the eluent and is subsequently recrystallized from n-hexane/diethyl ether. There is obtained isopropyl 2-chloro-4-fluoro-5-[2-methoxy-6-oxo-4-trifluoromethyl-1(6H)-pyrimidinyl]-benzoate, m.p. 121°-123° C.

A solution of 5 g of isopropyl 2-chloro-4-fluoro-5-[2-methoxy-6-oxo-4-trifluoromethyl-1(6H)-pyrimidinyl]-benzoate in 20 ml of methylene chloride is treated while stirring and cooling at 20°-25° C. with 25 ml of concentrated sulphuric acid. The reaction mixture is stirred at room temperature for 20 minutes and poured onto 100 g of ice. The orqanic phase is separated, the aqueous phase is extracted twice with 15 ml of ethyl acetate each time and the combined organic phases are washed to neutrality with water. Subsequently, the solution is dried over anhydrous sodium sulphate and evaporated to dryness under reduced pressure. The resinous residue is recrystallized from diethyl ether/ n-hexane. There is obtained 2-chloro-4-fluoro-5-[2-methoxy-6-oxo-4-trifluoromethyl-1(6H)-pyrimidinyl]-benzoic acid, m.p. 205°-210° C.

EXAMPLES 68 -71

Isopropyl 2-chloro-5-[3,6-dihydro-2,6-dioxo-3-methyl-4-substituted-1(2H)-pyrimidinyl]-4-fluorobenzoate and isopropyl 2-chloro-4-fluoro-5-[2-methoxy-4-oxo-4-substituted-1(6H)-pyrimidinyl]-benzoate are hydrolyzed analogously to the 4th part of Example 67 in order to produce the starting materials of formulae III and IIIa (benzoic acids) set forth in Table 8 hereinafter. The respective isopropyl benzoates have already been published in European patent publication No. 195,346 and 260,621, respectively.

TABLE 8

III′

R$^5$—N(CH$_3$)—C(=O)—N—[benzene ring with COOH, F, Cl substituents]

IIIa′

R$^5$—N=C(OCH$_3$)—N—[benzene ring with COOH, F, Cl substituents]

| Example | Example No(s). of end product I or Ia | Formula | R$^5$ | Physical data |
|---|---|---|---|---|
| 68 | 1-11, 20-26, 32-56 | III′ | CF$_3$ | M.p. 239-242° C. |
| 69 | 12, 13, 28-30, 60 | III′ | CH$_3$ | M.p. 236-239° C. |
| 70 | 27, 57-59 | III′ | C$_2$F$_5$ | M.p. 229-231° C. |
| 71 | 64-66 | IIIa′ | C$_2$F$_5$ | M.p. 197-199° C. |

EXAMPLE 72

The 2-chloro-5-[3-difluoromethyl-3,6-dihydro-2,6-dioxo-4-methyl-1(2H)-pyrimidinyl]-4-fluorobenzoic acid used as the starting material in Examples 14 and 31 can be produced as follows:

103 g of chlorodifluoromethane are introduced while stirring at 80° C. during 6 hours into a suspension of 145.0 g of isopropyl 2-chloro-4-fluoro-5-[3,6-dihydro-4-methyl-2,6-dioxo-1(2H)-pyrimidinyl]-benzoate and 59.0 g of anhydrous, finely powdered potassium carbonate in 1 l of dimethylformamide. After cooling the solid constituent is filtered off under suction and rinsed with 100 ml of dimethylformamide. The filtrate is concentrated to a large extent under reduced pressure at 55° C. the residue is poured into 2 l of water and the aqueous mixture is adjusted to pH 3 with concentrated hydrochloric acid. The mixture is extracted with 1.5 l of ethyl acetate and the organic phase is washed twice with 1 l of water eaoh time, dried over anhydrous sodium sulphate and evaporated to dryness under reduced pressure. The resinous residue is purified by chromatography on a silica gel column using ethyl acetate/n-hexane (1:1) as the eluent. The product is dissolved in 1500 ml of hot n-hexane and the solution is treated with charcoal, filtered and concentrated to 700 ml at an elevated temperature. Subsequently, it is seeded and cooled to 5° C. while stirring. The resulting crystals are filtered off under suction, washed with n-hexane and dried. There is obtained isopropyl 2-chloro-5-[3-difluoro-methyl-3,6-dihydro-4-methyl-2,6-dioxo-1(2H)-pyrimidinyl]-4-fluorobenzoate, m.p. 90°-93° C.

A solution of 18.0 g of isopropyl 2-chloro-5-[3-difluoromethyl-3,6-dihydro-4-methyl-2,6-dioxo-1(2H)-pyrimidinyl]-4-fluorobenzoate in 60 ml of methylene chloride is stirred intensively for 5 minutes with 100 ml of concentrated sulphuric acid and subsequently poured onto 1 kg of ice. The resulting crystals are filtered off under suction, washed twice with 50 ml of water each time and dissolved in 300 ml of methanol. The mother liquor is extracted twice with 100 ml of methylene chloride each time and the organic phase is washed to neutrality with water and combined with the methanolic solution. This solution is dried over anhydrous sodium sulphate and evaporated to dryness. The crystalline residue is suspended with 100 ml of ethyl acetate at 70° C. and cooled to room temperature, and the crystals are filtered off under suction and washed with diethyl ether. There is obtained 2-chloro-5-[3-difluoromethyl-3,6-dihydro-4-methyl-2,6-dioxo-1(2H)-pyrimidinyl]-4-fluorobenzoic acid, m.p. 247°-248° C.

III. Formulation Examples:

EXAMPLE 73

An emulsifiable concentrate contains the following ingredients:

| | |
|---|---|
| Compound in accordance with the invention (active substance) | 50 g/l |
| N-Methylpyrrolidone (1st solvent) | 200 g/l |
| Nonylphenol-(10) ethoxylate (non-ionic emulsifier) | 50 g/l |
| Calcium dodecylbenzenesulphonate (anionic emulsifier) | 25 g/l |
| Mixture of alkylbenzenes (2nd solvent) | ad 1000 ml |

The active substance and the emulsifiers are dissolved in the 1st solvent while stirring and the solution is made up to 1 litre with the 2nd solvent.

The resulting emulsifiable concentrate can be emulsified in water and then gives a ready-for-use spray liquor having the desired concentration.

EXAMPLE 74

An emulsifiable concentrate for compounds in accordance with the invention which have a good solubility contains the following ingredients:

| | |
|---|---|
| Compound in accordance with the invention (active substance) | 250 g/l |
| Oleyl alcohol polyethoxylate (about 1 mol of alcohol: 10 mol of $C_2H_4O$; non-ionic emulsifier) | 50 g/l |
| Calcium dodecylbenzenesulphonate (anionic emulsifier) | 25 g/l |
| Mixture of alkylbenzenes (solvent) | ad 1000 ml |

The active substance and the emulsifiers are dissolved in a portion of the solvent while stirring and the solution is made up to 1 litre with the remaining solvent.

The resulting emulsifiable concentrate can be emulsified in water and then gives a ready-for-use spray liquor having the desired concentration.

EXAMPLE 75

For the manufacture of a 25% spray powder the ingredients listed hereinafter are mixed with one another:

| | |
|---|---|
| Compound in accordance with the invention (active substance) | 25 g |
| Silicic acid, hydrated (carrier material, grinding aid) | 5 g |
| Sodium lauryl sulphate (wetting agent) | 1 g |
| Sodium lignosulphonate (dispersing agent) | 2 g |
| Kaolin (carrier material) | 67 g |
| | 100 g |

Subsequently, the mixture is finely milled using a pinned disc mill or comparable milling aggregate.

Upon stirring in water the resulting spray powder gives a fine suspension which is suitable as a ready-for-use spray liquor.

We claim:

1. A compound of the formula

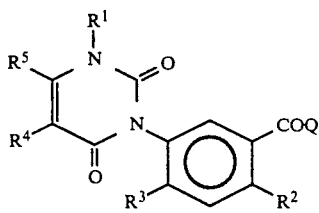

wherein
$R^1$ signifies hydrogen, $C_{1-4}$-alkyl, $C_{1-4}$-haloalkyl, $C_{2-5}$-alkenyl or $C_{3-5}$-alkynyl,
$R^2$ signifies halogen or cyano,
$R^3$ signifies hydrogen or halogen,
$R^4$ signifies hydrogen, halogen or $C_{1-4}$-alkyl,
$R^5$ signifies $C_{1-4}$-alkyl or, where $R^1$ is different from $C_{1-4}$-haloalkyl, also $C_{1-4}$-haloalkyl Q signifies one of the groups (a) to (d) (where $R^1$ is different from hydrogen) or a group (c) or (d) (where $R^1$ stands for hydrogen)

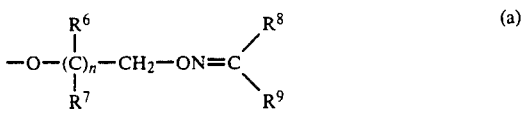

wherein
$R^6$ signifies hydrogen or $C_{1-4}$-alkyl,
$R^7$ signifies hydrogen, $C_{1-4}$-alkyl, phenyl or benzyl,
$R^8$ signifies hydrogen or $C_{1-6}$-alkyl,
$R^9$ signifies $C_{1-6}$-alkyl, $C_{3-6}$-cycloalkyl or phenyl. or
$R^8$ and $R^9$ together signify tri-, tetra-, penta- or hexamethylene,
n signifies 0 or 1,
$R^{10}$ signifies $C_{1-6}$-alkyl, $C_{1-6}$-alkylthio, $C_{2-7}$-alkoxycarbonyl or $C_{2-7}$-alkoxycarbonyl-$C_{1-4}$-alkyl,
$R^{11}$ signifies $C_{1-6}$-alkyl, trifluoromethyl, $C_{1-6}$-alkoxy-$C_{1-4}$-alkyl, $C_{2-7}$-alkoxycarbonyl-$C_{1-4}$-alkyl, di ($C_{2-7}$-alkoxycarbonyl)-$C_{1-4}$-alkyl, $C_{3-6}$-cycloalkyl, $C_{1-6}$-alkoxy, $C_{1-6}$-alkylthio, $C_{2-7}$-alkanoyl, $C_{2-7}$-alkoxycarbonyl, phenyl or 2-furyl,
or
$R^{10}$ and $R^{11}$ together with the carbon atom to which they are attached signify a cyclopentane or cyclohexane ring optionally substituted with 1 to 3 $C_{1-4}$-alkyl groups,
$R^{12}$ signifies $C_{1-8}$-haloalkyl, $C_{3-5}$-haloalkenyl or $C_{3-5}$-haloalkynyl,
and
$R^{13}$ signifies hydrogen, $C_{1-8}$-alkyl, $C_{3-8}$-alkenyl, $C_{3-8}$-alkynyl, $C_{2-6}$-alkoxyalkyl or $C_{3-8}$-cycloalkyl, phenyl or benzyl optionally
substituted with 1 to 3 $C_{1-4}$-alkyl groups, and the enol ethers of those compounds of formula I in which $R^1$ signifies $C_{1-4}$-alkyl, $C_{2-5}$-alkenyl or $C_{3-5}$-alkynyl and Q signifies a group (b), (c) or (d) as well as salts of those compounds of formula I and of the enol ethers in which $R^1$ and/or signifies hydrogen.

2. A compounds of claim 1, wherein $R^9$ is different from $C_{3-6}$-cycloalkyl and $R^{11}$ is different from phenyl.

3. A compound of to claim 1 wherein $R^1$ signifies straight-chain $C_{1-4}$-alkyl, $C_{1-4}$-haloalkyl.

4. A compound of any one of claims 1 to 3, wherein $R^2$ signifies chlorine or bromine and $R^3$ signifies hydrogen or fluorine.

5. A compound of claim 1 wherein $R^4$ signifies hydrogen, fluorine or methyl.

6. Compounds according to any one of claim 1, wherein $R^5$ signifies methyl, trifluoromethyl or pentafluoroethyl.

7. A compound according to claim 1, selected from 2-[(isopropylideneamino)oxy]-ethyl 2-chloro-5-[3,6-dihydro-2,6-dioxo-3-methyl-4-trifluoromethyl-1(2H)-pyrimidinyl]-4-fluorobenzoate,
2-[(cyclohexylideneamino)oxy]-ethyl 2-chloro-5-[3,6-dihydro-2,6-dioxo-3-methyl-4-trifluoromethyl-1(2H)-pyrimidinyl]-4-fluorobenzoate, α-{[(isopropylideneamino)oxy]methyl}-benzyl-2-chloro-5-[3,6-dihydro-2,6-dioxo-3-methyl-4-trifluoromethyl-1(2H)-pyrimidinyl]-4-fluorobenzoate, 1-cyclopropyl-1-ethanone O-{2-chloro-5-[3,6-dihydro2,6-dioxo-3-methyl-4-trifluoromethyl-1(2H)-pyrimidinyl]-4-fluorobenzoy1}oxime, 1-[4-chloro-2-fluoro-5-{[(isopropylideneamino)oxy]-carbonyl}-phenyl]-3-methyl-4-trifluoromethyl-2,6(1H,3H)-pyrimidinedione.

2-furyl methyl ketone O-{2-chloro-5-[3,6-dihydro-2,6-dioxo-3-methyl-4-trifluoromethyl-1(2H)-pyrimidinyl]-4-fluorobenzoyl]oxime, 2,3-butanedione 2-[O-[2-chloro-5-[3,6-dihydro-2,6-dioxo-3-methyl-4-trifluoromethyl-1(2H)-pyrimidinyl]-4-fluorobenzoyl]}oxime, 2-fluoro-1-fluoromethylethyl 2-chloro-4-fluoro-5-[2-methoxy-6 oxo-4-trifluoromethyl-1(6H)-pyrimidinyl]-benzoate, 2-chloroethyl 2-chloro-4-fluoro-5-[2-methoxy-6-oxo-4-trifluoromethyl-1(6H)-pyrimidinyl]-benzoate, 2-fluoroethyl 2-chloro-5-[3,6-dihydro-2,6-dioxo-3-methyl-4-trifluoromethyl-1(2H)-pyrimidinyl]-4-fluorobenzoate 3-chloro-2-butenyl 2-chloro-4-fluoro-5-[2-methoxy-6-oxo-4-trifluoromethyl-1(6H)-pyrimidinyl]-benzoate.

3-chloro-2-butenyl 2-chloro-5-[3,6-dihydro-2,6-dioxo-3-methyl-4-trifluoromethyl-1(2H)-pyrimidinyl]-4-fluorobenzoate, 2-fluoroethyl 2-chloro-4-fluoro-5-[2-methoxy-6-oxo-4-trifluoromethyl-1(6H)-pyrimidinyl]-benzoate, S-isopropyl 2-chloro-5-[3,6-dihydro-2,6-dioxo-3-methyl-4-trifluoromethyl-1(2H)-pyrimidinyl]-4-fluoro-thiobenzoate, S-ethyl 2-chloro-5-[3,6-dihydro-2,6-dioxo-3-methyl-4-trifluoromethyl-1(2H)-pyrimidinyl]-4-fluorothiobenzoate, S-(n-butyl) 2-chloro-5-[3,6-dihydro-2,6-dioxo-3-methyl-4-trifluoromethyl-1(2H)-pyrimidinyl]-4-fluorothiobenzoate.

S-allyl 2-chloro-5-[3,6-dihydro-2,6-dioxo-3-methyl-4-trifluoromethyl-1(2H)-pyrimidinyl]-4-fluorothiobenzoate, S-cyclohexyl 2-chloro-5-[3,6-dihydro-2,6-dioxo-3-methyl-4-trifluoromethyl-1(2H)-pyrimidinyl]-4-fluorothiobenzoate, S-phenyl 2-chloro-5-[3,6-dihydro-2,6-dioxo-3-methyl-4-trifluoromethyl-1(2H)-pyrimidinyl]-4-fluoro-thiobenzoate, S-benzyl 2-chloro-5-[3,6-dihydro-2,6-dioxo-3-methyl-4-trifluoromethyl-1(2H)-pyrimidinyl]-4-fluorothiobenzoate and S-isopropyl 2-chloro-5-[3,6-dihydro-3.4-dimethyl-2,6-dioxo-1(2H)-pyrimidinyl]-4-fluorothiobenzoate.

8. A compound of claim 1 wherein $R^1$ is methyl or difluoromethyl.

9. A weed control composition, which contains an effective amount of at least one compound of the general formula

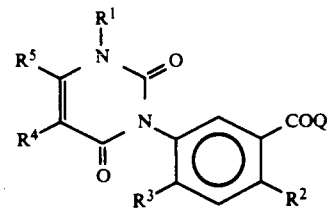

wherein
$R^1$ signifies hydrogen, $C_{1-4}$-alkyl, $C_{1-4}$-haloalkyl, $C_{2-5}$-alkenyl or $C_{3-5}$-alkynyl,
$R^2$ signifies halogen or cyano,
$R^3$ signifies hydrogen or halogen,
$R^4$ signifies hydrogen, halogen or $C_{1-4}$-alkyl,
$R^5$ signifies $C_{1-4}$-alkyl or, where $R^1$ is different from $C_{1-4}$-haloalkyl, also $C_{1-4}$-haloalkyl and
Q signifies one of the groups (a) to (d) (where $R^1$ is different from hydrogen) or a group (c) or (d) (where $R^1$ stands for hydrogen)

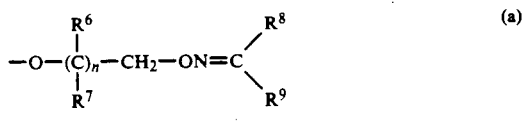

wherein
$R^6$ signifies hydrogen or $C_{1-4}$-alkyl,
$R^7$ signifies hydrogen, $C_{1-4}$-alkyl, phenyl or benzyl,
$R^8$ signifies hydrogen or $C_{1-6}$-alkyl,
$R^9$ signifies $C_{1-6}$-alkyl, $C_{3-6}$-cycloalkyl or phenyl. or
$R^8$ and $R^9$ together signify tri-, tetra-, penta- or hexamethylene,
n signifies 0 or 1,
$R^{10}$ signifies $C_{1-6}$-alkyl, $C_{1-6}$-alkylthio, $C_{2-7}$-alkoxycarbonyl or $C_{2-7}$-alkoxycarbonyl-$C_{1-4}$-alkyl,
$R^{11}$ signifies $C_{1-6}$-alkyl, trifluoromethyl, $C_{1-6}$-alkoxy-$C_{1-4}$-alkyl, $C_{2-7}$-alkoxycarbonyl-$C_{1-4}$-alkyl, di ($C_{2-7}$-alkoxycarbonyl)-$C_{1-4}$-alkyl, $C_{3-6}$-cycloalkyl, $C_{1-6}$-alkoxy, $C_{1-6}$-alkylthio, $C_{2-7}$-alkanoyl, $C_{2-7}$-alkoxycarbonyl, phenyl or 2-furyl,
$R^{10}$ and $R^{11}$ and together with the carbon atom to which they are attached signify a cyclopentane or cyclohexane ring optionally substituted with 1 to 3 $C_{1-4}$-alkyl groups,
$R^{12}$ signifies $C_{1-8}$-haloalkyl, $C_{3-5}$-haloalkenyl or $C_{3-5}$-haloalkynyl, and
$R^{13}$ signifies hydrogen, $C_{1-8}$-alkyl, $C_{3-8}$-alkenyl. $C_{3-8}$-alkYnyl, $C_{2-6}$-alkoxyalkyl or $C_{3-8}$-cycloalkyl, phenyl or benzyl optionally substituted with 1 to 3 $C_{1-4}$-alkyl groups, or of an enol ether of such a compound of formula I in which $R^1$ signifies $C_{1-4}$-alkyl, $C_{2-5}$-alkenyl or $C_{3-5}$-alkynyl and Q signifies a group (b), (c) or (d) or of a salt of such a compound of formula I or of such an enol ether in which $R^1$ and/or $R^{13}$ signifies hydrogen, and a carrier.

10. A weed control composition of claim 9, in which $R^9$ is different from $C_{3-6}$-cycloalkyl and $R^{11}$ is different from phenyl.

11. A weed control composition, which contains an effective amount of at least one compound selected from the group

- 2-[(isopropylideneamino)oxy]-ethyl 2-chloro-5-[3,6-dihydro-2,6-dioxo-3-methyl-4-trifluoromethyl-1(2H)-pyrimidinyl]-4-fluorobenzoate,
- 2-[(cyclohexylideneamino)oxy]-ethyl 2-chloro-5-[3,6-dihydro-2,6-dioxo-3-methyl-4-trifluoromethyl-1(2H)-pyrimidinyl]-4-fluorobenzoate,
- α-{[(isopropylideneamino)oxy]methyl}-benzyl-2-chloro-5-[3,6-dihydro-2,6-dioxo-3-methyl-4-trifluoromethyl-1(2H)-pyrimidinyl]-4-fluorobenzoate,
- 1-cyclopropyl-1-ethanone O-{2-chloro-5-[3,6-dihydro2,6-dioxo-3-methyl-4-trifluoromethyl-1(2H)-pyrimidinyl]-4-fluorobenzoy 1}oxime,
- 1-[4-chloro-2-fluoro-5-{[(isopropylideneamino)oxy]-carbonyl}-phenyl]-3-methyl-4-trifluoromethyl-2,6(1H,3H)-pyrimidinedione.
- 2-furyl methyl ketone O-{2-chloro-5-[3,6-dihydro-2,6-dioxo-3-methyl-4-trifluoromethyl-1(2H)-pyrimidinyl]-4-fluorobenzoyl]oxime,
- 2,3-butanedione 2-[O-[2-chloro-5-[3,6-dihydro-2,6-dioxo-3-methyl-4-trifluoromethyl-1(2H)-pyrimidinyl]-4-fluorobenzoyl}]oxime,
- 2-fluoro-1-fluoromethylethyl 2-chloro-4-fluoro-5-[2-methoxy-6 oxo-4-trifluoromethyl-1(6H)-pyrimidinyl]-benzoate,
- 2-chloroethyl 2-chloro-4-fluoro-5-[2-methoxy-6-oxo-4-trifluoromethyl-1(6H)-pyrimidinyl]-benzoate,
- 2-fluoroethyl 2-chloro-5-[3,6-dihydro-2,6-dioxo-3-methyl-4-trifluoromethyl-1(2H)-pyrimidinyl]-4-fluorobenzoate
- 3-chloro-2-butenyl 2-chloro-4-fluoro-5-[2-methoxy-6-oxo-4-trifluoromethyl-1(6H)-pyrimidinyl]-benzoate.
- 3-chloro-2-butenyl 2-chloro-5-[3,6-dihydro-2,6-dioxo-3-methyl-4-trifluoromethyl-1(2H)-pyrimidinyl]-4-fluorobenzoate,
- 2-fluoroethyl 2-chloro-4-fluoro-5-[2-methoxy-6-oxo-4-trifluoromethyl-1(6H)-pyrimidinyl]-benzoate,
- S-isopropyl 2-chloro-5-[3,6-dihydro-2,6-dioxo-3-methyl-4-trifluoromethyl-1(2H)-pyrimidinyl]-4-fluoro-thiobenzoate,
- S-ethyl 2-chloro-5-[3,6-dihydro-2,6-dioxo-3-methyl-4-trifluoromethyl-1(2H)-pyrimidinyl]-4-fluorothiobenzoate,
- S-(n-butyl) 2-chloro-5-[3,6-dihydro-2,6-dioxo-3-methyl-4-trifluoromethyl-1(2H)-pyrimidinyl]-4-fluorothiobenzoate.
- S-allyl 2-chloro-5-[3,6-dihydro-2,6-dioxo-3-methyl-4-trifluoromethyl-1(2H)-pyrimidinyl]-4-fluorothiobenzoate,
- S-cyclohexyl 2-chloro-5-[3,6-dihydro-2,6-dioxo-3-methyl-4-trifluoromethyl-1(2H)-pyrimidinyl]-4-fluorothiobenzoate,
- S-phenyl 2-chloro-5-[3,6-dihydro-2,6-dioxo-3-methyl-4-trifluoromethyl-1(2H)-pyrimidinyl]-4-fluorothiobenzoate,
- S-benzyl 2-chloro-5-[3,6-dihydro-2,6-dioxo-3-methyl-4-trifluoromethyl-1(2H)-pyrimidinyl]-4-fluorothiobenzoate and
- S-isopropyl 2-chloro-5-[3,6-dihydro-3.4-dimethyl-2,6-dioxo-1(2H)-pyrimidinyl]-4-fluorothiobenzoate and a carrier.

* * * * *